United States Patent
Chodobski et al.

(10) Patent No.: US 9,921,230 B2
(45) Date of Patent: Mar. 20, 2018

(54) METHODS FOR DIAGNOSIS AND TREATMENT OF CONCUSSION OR BRAIN INJURY

(71) Applicant: Rhode Island Hospital, Providence, RI (US)

(72) Inventors: Adam Chodobski, Providence, RI (US); Joanna Szmydynger-Chodobska, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 14/879,012

(22) Filed: Oct. 8, 2015

(65) Prior Publication Data
US 2016/0103140 A1   Apr. 14, 2016

Related U.S. Application Data

(60) Provisional application No. 62/061,374, filed on Oct. 8, 2014.

(51) Int. Cl.
*G01N 33/53* (2006.01)
*G01N 33/68* (2006.01)

(52) U.S. Cl.
CPC ..... *G01N 33/6896* (2013.01); *G01N 33/6893* (2013.01); *G01N 2333/4724* (2013.01); *G01N 2333/575* (2013.01); *G01N 2333/96494* (2013.01); *G01N 2800/28* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 6,719,971 B1 | 4/2004 | Carter et al. | |
| 2009/0093488 A1* | 4/2009 | Buck | G01N 33/574 514/249 |
| 2009/0226396 A1* | 9/2009 | Haley | G01N 33/5011 424/85.2 |
| 2012/0219943 A1* | 8/2012 | Ky | G01N 33/6893 435/6.11 |
| 2015/0133521 A1* | 5/2015 | Bloch | C12N 15/113 514/44 A |
| 2015/0346222 A1* | 12/2015 | Bergmann | G01N 33/74 506/9 |

OTHER PUBLICATIONS

Kleindienst et al. Acta Neurochirurgica Supplementum 2010 vol. 106, p. 221-224.*
Dong et al. The Journal of Trauma 2011 vol. 71, p. 1194-1198.*
Chodobski et al., CNS Barriers in Neurotrauma. In: Vascular Mechanisms in CNS Trauma. Edited by Lo et al., Springer, New York, 2014, pp. 3-28.
Dong et al., Copeptin is associated with mortality in patients with traumatic brain injury. J Trauma. Nov. 2011;71(5):1194-8.
Hadass et al., Selective inhibition of matrix metalloproteinase-9 attenuates secondary damage resulting from severe traumatic brain injury. PLoS One. Oct. 23, 2013;8(10):e76904.
Liu et al., Normobaric hyperoxia attenuates early blood-brain barrier disruption by inhibiting MMP-9-mediated occludin degradation in focal cerebral ischemia. J Neurochem. Feb. 2009;108(3):811-20.
Shahim et al., Blood biomarkers for brain injury in concussed professional ice hockey players. JAMA Neurol. Jun. 2014;71(6):684-92.
Shan et al., A New Panel of Blood Biomarkers for the Diagnosis of Mild Traumatic Brain Injury/Concussion in Adults. J Neurotrauma. Jan. 1, 2016;33(1):49-57.
Siman et al., Evidence That the Blood Biomarker SNTF Predicts Brain Imaging Changes and Persistent Cognitive Dysfunction in Mild TBI Patients. Front Neurol. Nov. 18, 2013;4:190.

* cited by examiner

*Primary Examiner* — Changhwa J Cheu
(74) *Attorney, Agent, or Firm* — Mintz Levin Cohn Ferris Glovsky and Popeo, P.C.; Ingrid A. Beattie

(57) ABSTRACT

This invention relates to compositions and methods for diagnosing and treating concussion/mTBI.

19 Claims, 4 Drawing Sheets

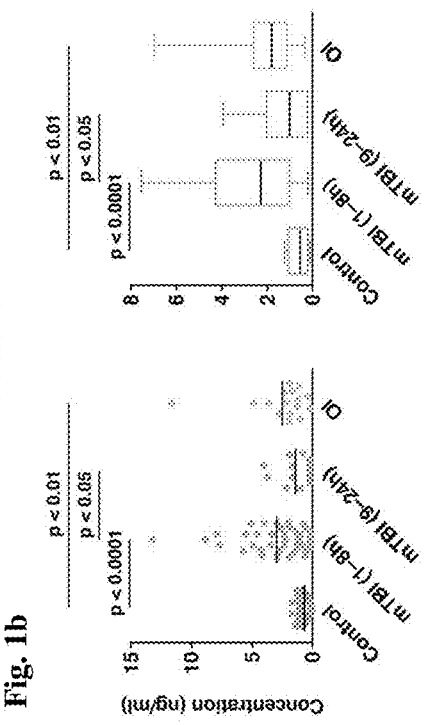
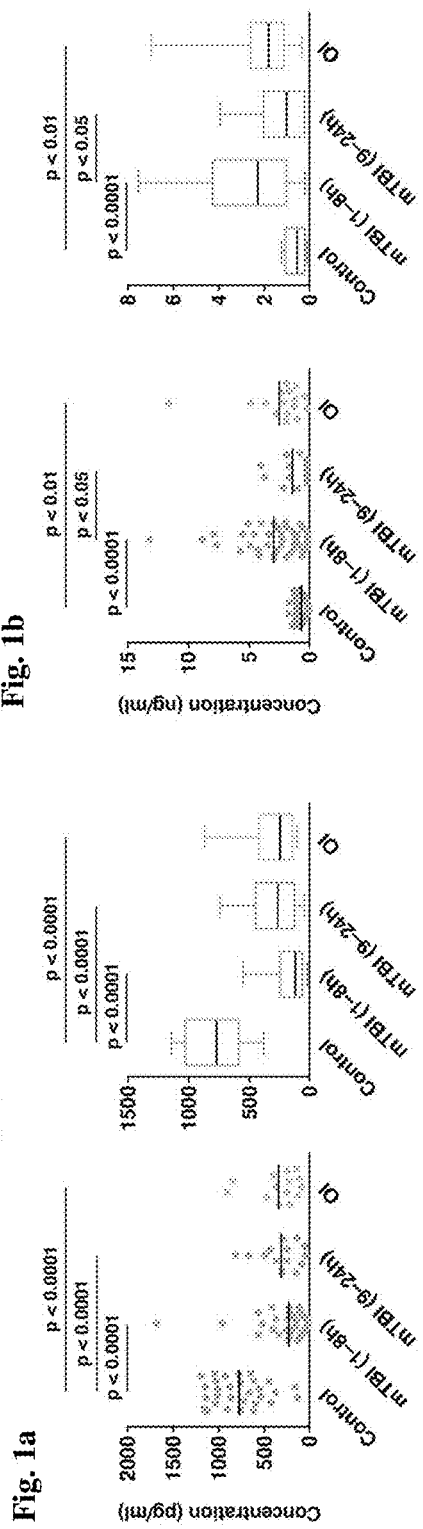
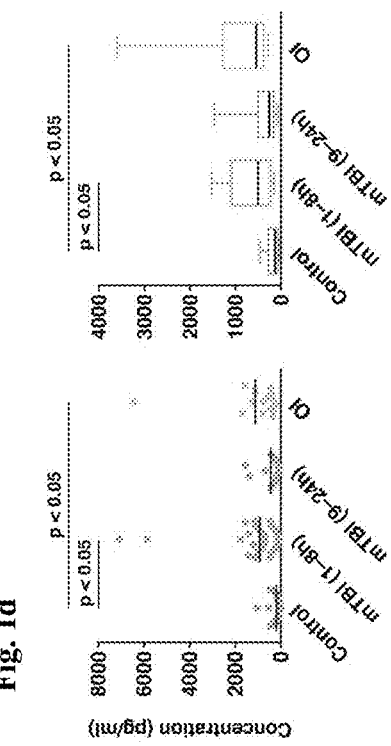
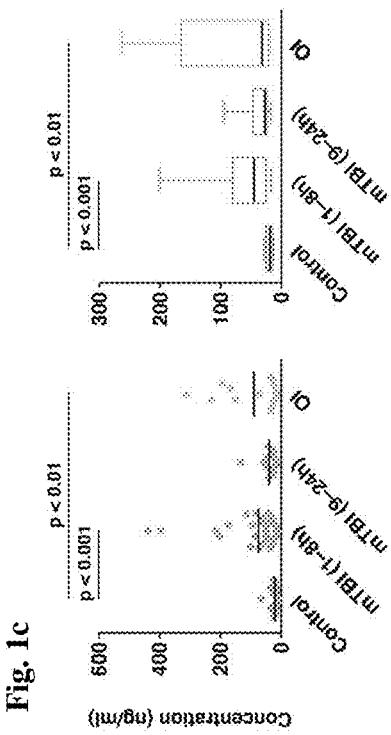

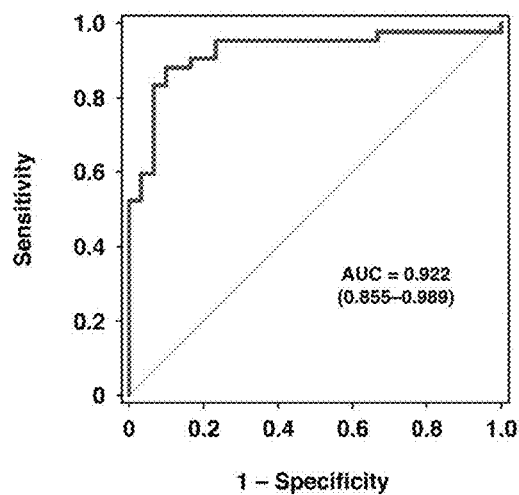
Fig. 2a Copeptin
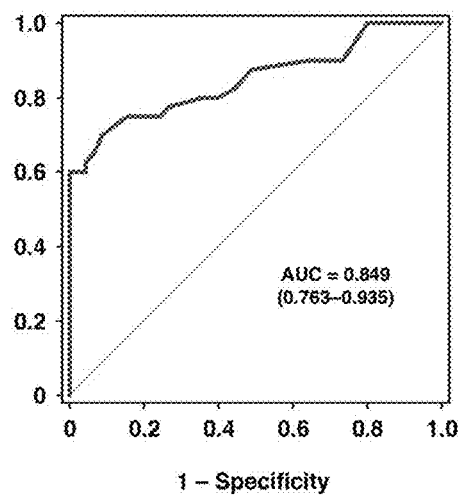
Fig. 2b LGALS3
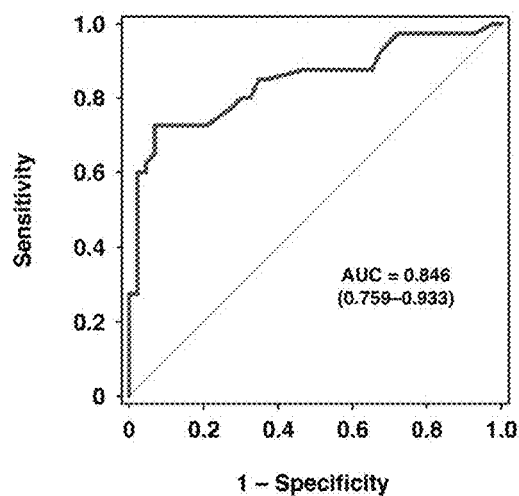
Fig. 2c MMP9
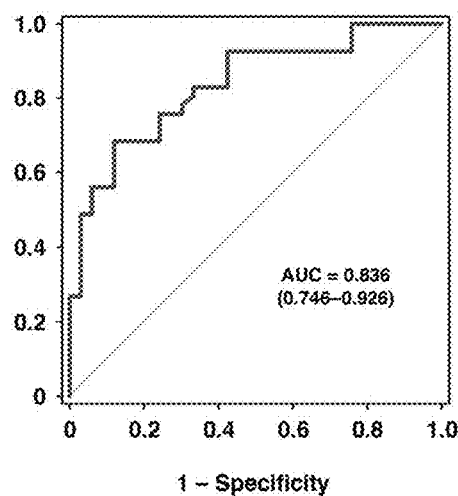
Fig. 2d OCLN

METHODS FOR DIAGNOSIS AND TREATMENT OF CONCUSSION OR BRAIN INJURY

RELATED APPLICATIONS

This application claims the priority and benefit of U.S. Ser. No. 62/061,374 filed Oct. 8, 2014, the contents of which are incorporated by reference in their entireties.

INCORPORATION-BY-REFERENCE

The contents of the text file named "21486-624001US_ST25.txt", which is created on Oct. 6, 2015 and is 14.2 KB in size, are hereby incorporated by reference in their entireties.

FIELD OF THE INVENTION

The invention relates to brain injury.

BACKGROUND OF THE INVENTION

Traumatic Brain Injury (TBI) is one of the major public health and socioeconomic problems in both developed and developing countries. In the US alone, an estimated 1.7 million civilians sustain TBI each year, and in Europe, an average aggregate hospitalization and fatal TBI incidence rate of 235 per 100,000 people per year has been reported. Most TBI cases (70-90%) are classified as mild traumatic brain injury (mTBI), which is often synonymous with concussion. Globally, the incidence of hospital-treated patients with mTBI is 100-300 per 100,000 people per year. However, it has been estimated that the actual population-based rate of mTBI is likely to be above 600 per 100,000 people because many individuals sustaining an mTBI do not seek the hospital treatment or do not report the injury. In the military, it has been estimated that 5-35% of American service members deployed to Iraq and Afghanistan sustained an mTBI, with 80% of these injuries being secondary to blast exposures.

mTBI represents a significant diagnostic challenge. Current diagnosis is subjective and frequently based on self-reported neurological symptoms, some of which could be ignored, concealed, or overstated. This problem is especially magnified in children, as they may have trouble in recognizing and/or defining their symptoms. Accordingly, there is a great need to identify biomarkers that would provide physicians with objective tools for the diagnosis of patients sustaining concussions.

SUMMARY OF THE INVENTION

Provided herein is a method for identifying concussion or traumatic brain injury (e.g., isolated concussion, mild traumatic brain injury) in a subject. The method includes steps of (1) providing a test sample from a subject, where the sample includes a processed bodily fluid; (2) performing a reaction in vitro by contacting the test sample with a binding agent to yield a complex including the binding agent and a protein selected from the group consisting of copeptin, matrix metalloproteinase 9 (MMP9), lectin, galactoside-binding, soluble, 3 (LGALS3), and occludin (OCLN); and (3) detecting the complex, where a decrease in the level of the complex that includes a copeptin binding agent such as a copeptin-specific antibody and copeptin compared to a normal control and an increase in the level of the complex that includes (i) a MMP9 binding agent such as a MMP9-specific antibody and MMP9, (ii) an LGALS3 binding agent such as an LGALS3-specific antibody and LGALS3, or (iii) an OCLN binding agent such as an OCLN-specific antibody and OCLN compared to a normal control indicates concussion or traumatic brain injury in the subject.

In some cases, the binding agent includes a plurality of binding agents including a first binding agent that binds to copeptin, a second binding agent that binds to MMP9, a third binding agent that binds to LGALS3, and a fourth binding agent that binds to OCLN.

In some cases, the binding agent includes a plurality of binding agents that bind to at least two proteins selected from the group consisting of copeptin, MMP9, LGALS3, and OCLN.

In some cases, the binding agent includes a plurality of binding agents that bind to at least three proteins selected from the group consisting of copeptin, MMP9, LGALS3, and OCLN.

In some cases, the binding agent includes a plurality, e.g., 4 binding agents, each of which is specific for one of MMP9, LGLS3, OCLN, and copeptin. For example, the binding agents are immobilized on a solid substrate and act to capture and immobilize one, two, three or all four of the above-listed markers onto the solid surface/substrate.

The bodily fluid is removed from the individual to be tested and processed to remove cells and/or clotting components from the fluid. An exemplary bodily fluid includes, but is not limited to, blood, plasma, serum, lymph, breast milk, saliva, mucous, cellular extracts, cerebrospinal fluid, or urine. Preferably, the bodily fluid is plasma.

The method is particularly advantageous, because it reliably detects concussion/mTBI soon after an injury has occurred, and it utilizes a small amount of test sample. For example, the accuracy of the method described herein is about 80%, 85%, 90%, 91%, 92%, 93%, 94%, 95%, 96%, 97%, 98%, 99% or higher. For example, a reliable diagnosis is made using fluid that is derived from a patient within about 0.1, 0.5, 1, 2, 5, 6, 8 hours or more (e.g., about 12 hours, 24 hours, 48 hours or more) of a head injury. However, the surprising advantage of the method is the high level of accuracy of identifying concussion in an individual using the 4 described indices very shortly following a head insult, thereby resulting implementation of therapeutic intervention within hours. Such a diagnostic and therapeutic protocol leads to improved clinical outcomes of the injured subject. For example, a difference (e.g., increase or decrease) of 10%, 20%, 50%, 75%, 2-fold, 5-fold, 10-fold or more between a patient-associated level of a biomarker and a normal level, e.g., level obtained from an injured individual is useful to diagnose concussion. For example, only a small volume from about 10 ul to about 200 µl (e.g., about 10, 20, 30, 40, 50, 60, 70, 80, 90, 100, 110, 120, 130, 140, 150, 160, 170, 180, 190, or 200 µl) of blood sample is sufficient for an accurate determination.

Any binding agent that binds to copeptin, MMP9, LGALS3 or OCLN can be used in the methods described herein, for example, an antibody or a fragment thereof, a detectable protein or a fragment thereof. The antibody can be a polyclonal antibody or a monoclonal antibody. In some cases, the binding agent is bound to a solid support (e.g., a strip, a glass, a silicon, a polymer, a bead or a nanoparticle). In some cases, the antibody is conjugated to a detectable moiety. Exemplary detectable moiety includes, but is not limited to, a fluorescent marker (e.g., fluorescein isothiocyanate, rhodamine, phycoerythrin, phycocyanin, allophycocyanin, p-phthaldehyde and fluorescamine, and 152 Eu)

and a chemiluminescent compound (e.g., luminol, isoluminol, theromatic acridinium ester, imidazole, acridinium salt and oxalate ester). Other exemplary binding agents that can be used include, but are not limited to, DuoSet ELISA Development Systems from R&D Systems (Minneapolis, Minn.) for LGALS3 and MMP9 and the ELISA kits from USCN Life Science for OCLN and copeptin. In some examples, a first antibody is immobilized on a solid support and used as a capture reagent to immobilize the patient-derived marker, and a second antibody is used to label, detect and quantify the amount of the marker. The second antibody is optionally conjugated to a detectable label or such a detectable reagent that binds to the second antibody is used to quantify the level of marker.

In addition to diagnostic value, the proteins described above as biomarkers are useful in therapy to treat individuals having been diagnosed with concussion/mTBI. Accordingly, a method of treating concussion or traumatic brain injury is carried out by modulating the activity or level of a protein selected from the group consisting of copeptin, MMP9, LGALS3, and OCLN. For example, the method includes administering to a subject having concussion/mTBI a therapeutically effective amount of an MMP9 selective inhibitor (e.g., SB-3CT, SB-3CT prodrug or a pharmaceutically acceptable salt, ester, metabolite, polymorph or solvate thereof) or an LGALS3 selective inhibitor (e.g., N-acetyl-lactosamine, a glycomimetic compound, or a pharmaceutically acceptable salt, ester, prodrug, metabolite, polymorph or solvate thereof). Combinations of such modulators are also useful in therapeutic approaches.

Also provided herein is a diagnostic device that includes a solid support and a binding agent immobilized on the support, where the binding agent binds to a protein selected from the group consisting of copeptin, MMP9, LGALS3, and OCLN; or two, three or all four of the listed markers. Thus, also provided herein is a diagnostic device that includes a solid support and a plurality of immobilized binding agents on the support, where a first binding agent binds to copeptin, a second binding agent binds to MMP9, a third binding agent binds to LGALS3, or a fourth binding agent binds to OCLN.

Such device is portable, convenient and easy to operate, and it provides an accurate diagnosis result in a short period of time (e.g., within about 10, 20, 30, 40 minutes). Thus, this device can be used for determining concussion and mTBI in various locations and under various occasions, for example, at an accident site, in an ambulance, in an emergency room, on the field (e.g., battle field).

"Altered", "an increase" or "a decrease" refers to a detectable change or difference between the measured biomarker and the reference value from a reasonably comparable state, profile, measurement, or the like. One skilled in the art should be able to determine a reasonable measurable change. Such changes may be all or none. They may be incremental and need not to be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold, 2-fold, 3-fold, 4-fold, 5-fold, 7.5-fold, 10-fold or more, or any values in between 1-fold and 10-fold. The change may be statistically significant with a p value of 0.1, 0.05, 0.001, or 0.0001.

A "biomarker" used herein refers to a molecular indicator of a specific biological property; a biochemical feature or facet that can be used to detect colorectal cancer. "Biomarker" encompasses, without limitation, proteins, nucleic acids, and metabolites, together with their polymorphisms, mutants, isoform variants, related metabolites, derivatives, precursors including nucleic acids and pro-proteins, cleavage products, protein-ligand complexes, post-translationally modified variants (such as cross-linking or glycosylation), fragments, and degradation products, as well as any multi-unit nucleic acid, protein, and glycoprotein structures comprised of any of the biomarkers as constituent subunits of the fully assembled structure, and other analytes or sample-derived measures.

Polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. Purified also defines a degree of sterility that is safe for administration to a Human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules. cDNA is not naturally occurring.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The antibody is a polyclonal antisera or monoclonal antibody. The invention encompasses not only an intact monoclonal antibody, but also an immunologically-active antibody fragment, e.g., a Fab or (Fab)2 fragment; an engineered single chain FV molecule; or a chimeric molecule, e.g., an antibody which contains the binding specificity of one antibody, e.g., of murine origin, and the remaining portions of another antibody, e.g., of human origin. The antibody is a polyclonal antisera or monoclonal antibody.

As used herein, "treatment" is an approach for obtaining beneficial or desired results, including clinical results. For purposes of this disclosure, beneficial or desired clinical results include, but are not limited to, alleviation or amelioration of symptoms (e.g., amnesia, nausea, vomiting, headache, diplopia, dizziness, sleepiness, confusion, and/or disorientation/sensation of "fogginess"), diminishment of extent of head injury, stabilized (i.e., not worsening) state of head injury, delay or slowing of head injury progression, amelioration or palliation of the head injury state, and recovery (whether partial or total), whether detectable or undetectable.

The term "subject" as used herein includes all members of the animal kingdom prone to suffering from the indicated disorder. In some aspects, the subject is a mammal, and in some aspects, the subject is a human of general population. The methods are also applicable to companion animals such as dogs and cats as well as livestock such as cows, horses, sheep, goats, pigs, and other domesticated and wild animals. In some cases, the subject is suffering from one or more following symptoms: amnesia, nausea, vomiting, headache, diplopia, dizziness, sleepiness, confusion, disorientation, and sensation of "fogginess." In some cases, the subject is suffering from heart disease, hypertension, asthma, and/or other disease. In some cases, the subject is not suffering from long bone fracture, vertebral fracture, compartment syndrome, arterial bleeding, spinal cord injury, injuries to the lung, heart, and abdominal organs, ocular injuries, burns, or significant soft tissue injuries.

Other features and advantages of the invention will be apparent from the following description of the preferred embodiments thereof, and from the claims. All references cited herein are hereby incorporated by reference.

BRIEF DESCRIPTION OF THE DRAWINGS

FIGS. 1A-1D are scatter and box plots showing plasma levels of four biomarkers. The horizontal bars in the scatter plots represent means, whereas the vertical whiskers extending from box plots represent the $10^{th}$ and $90^{th}$ percentiles. The Kruskal-Wallis one-way analysis of variance was used followed by Dunn's test to compare the subgroups of mTBI patients with uninjured control subjects and patients with OI. Control=uninjured subjects. mTBI (1-8 h)=mTBI patients in whom blood samples were collected between 1 and 8 h post-injury. mTBI (9-24 h)=mTBI patients in whom blood samples were collected between 9 and 24 h post-injury. OI=subjects with orthopedic injury. FIG. 1A is for biomarker copeptin; FIG. 1B is for biomarker galectin 3 (LGALS3); FIG. 1C is for biomarker matrix metalloproteinase 9 (MMP9); and FIG. 1D is for biomarker occludin (OCLN).

FIGS. 2A-2F are line graphs showing ROC curves for candidate biomarkers. ROC analyses were conducted to assess the ability of candidate biomarkers to discriminate between mTBI patients (blood samples collected at 1-8 h post-injury) and uninjured subjects. The AUC values and their 95% confidence intervals (in parentheses) are shown for each biomarker. AUC=area under the curve. FIG. 2A is for biomarker copeptin; FIG. 2B is for biomarker LGALS3; FIG. 2C is for biomarker matrix MMP9; FIG. 2D is for biomarker OCLN; FIG. 2E is for the combination of copeptin and LGALS3; and FIG. 2F is for the combination of copeptin, LGALS3 and MMP9.

DETAILED DESCRIPTION

Figure 2E:
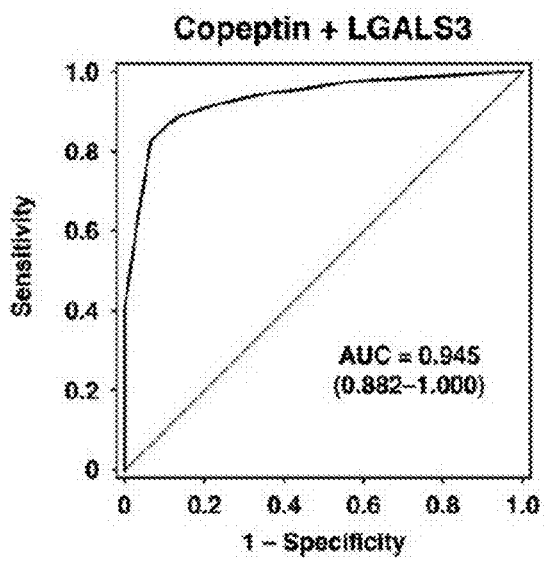

The invention described herein addresses the failure to date of any routine tests to objectively, quickly and accurately diagnose mild traumatic brain injury (mTBI)/concussion. Mild TBI (also known as concussion or minor brain injury or minor head injury or isolated concussion) is the most prevalent TBI (as demonstrated in Table 4), and it is often missed at time of initial injury. 15% of people with mild TBI have symptoms that last one year or more. Mild TBI is defined as the result of the forceful motion of the head or impact causing a brief change in mental status (confusion, disorientation or loss of memory) or loss of consciousness for less than 30 minutes. Common symptoms of mTBI include: fatigue, headaches, visual disturbances, memory loss, poor attention, sleep disturbances, dizziness, loss of balance, irritability-emotional disturbances, feelings of depression, seizure, nausea, loss of smell, sensitivity to light and sounds, mood changes, getting lost or confused, and slowness in thinking.

Unlike previously reported tests, which utilized proteins released from damaged neurons or glia (their expression levels are low and/or the assays used for their detection are complicated), the diagnostic test described herein for concussion/mTBI was developed based on a unique combination of plasma biomarkers with high accuracy. Surprisingly, such high accuracy is not affected by underlying disease that the subject is suffering from (such as asthma, heart disease, hypertension, etc.), further demonstrating the great specificity and sensitivity of these biomarkers in identifying mTBI. Blood plasma is a non-naturally occurring processed sample derived from blood, e.g., obtained by venipuncture, and is usually prepared by spinning a tube of fresh blood containing an anticoagulant in a centrifuge until the blood cells fall to the bottom of the tube. The blood plasma is then poured or drawn off.

Standard protocols are used to prepare a plasma sample. An illustrative protocol is described herein: collecting whole blood into commercially available anticoagulant-treated tubes e.g., EDTA-treated (lavender tops) or citrate-treated (light blue tops); and removing cells by centrifugation for 10 minutes at 1,000-2,000×g using a refrigerated centrifuge. Centrifugation for 15 minutes at 2,000×g depletes platelets in the plasma sample. The resulting supernatant is designated plasma. Following centrifugation, it is important to immediately transfer the liquid component (plasma) into a clean polypropylene tube using a Pasteur pipette. The samples should be maintained at 2-8° C. while handling. If the plasma is not analyzed immediately, the plasma should be apportioned into 0.5 ml aliquots, stored, and transported at −20° C. or lower. It is important to avoid freeze-thaw cycles. Samples which are hemolyzed, icteric, or lipemic can invalidate certain tests.

The compositions and methods described herein utilize a unique combination of plasma biomarkers and binding agents to detect those biomarkers, and biomarker/binding agent complexes that allow for the diagnosis of concussion. Synthesis of key proteins (copeptin, MMP9, LGALS3, and OCLN) is altered in response to mTBI. This alteration results in changes in blood levels of these proteins, which are detectable using a variety of assays. At least two of the biomarkers are useful as targets for therapeutic intervention in mTBI. The approach described herein is diametrically different from traditional approach of identifying blood biomarkers for mTBI, which focuses on central nervous system (CNS)-derived proteins released by damaged brain cells.

The compositions and methods described herein constitute a combination of biomarkers, which includes, but is not limited to, four families of proteins: copeptin, galectin 3 (encoded by gene lectin, galactoside-binding, soluble, 3 (LGALS3)), matrix metalloproteinase 9 (MMP9), occludin (OCLN), and any combination thereof. The panel of these markers discriminates patients with mTBI from uninjured subjects. In 90% of mTBI patients, the plasma levels of at least two biomarkers are changed beyond the cutoff values, whereas 0% of uninjured controls have the plasma levels of two biomarkers changed. Furthermore, since in mTBI patients there is a positive correlation between two of these biomarkers (OCLN and LGALS3), these biomarkers permit a definite diagnosis of suspected concussion in the presence of orthopedic injuries (OI).

Accordingly, provided herein is a method for identifying concussion or traumatic brain injury (e.g., mTBI or isolated concussion) in a subject. The method includes steps of (1) providing a test sample from a subject, where the sample includes a bodily fluid; (2) performing a reaction in vitro by contacting the test sample with a binding agent to yield a complex including the binding agent and a protein selected from the group consisting of copeptin, MMP9, LGALS3, or OCLN compared to a normal control indicates concussion or traumatic brain injury in the subject.

Two of the biomarkers described herein (MMP9 and LGALS3) also represent clinical targets, e.g., inhibition of MMP9 and LGALS3 leads to clinical improvement of a subject having been diagnosed with concussion.

The invention here also provides at least two (2, 3, or 4) biomarker selected from the group consisting of copeptin, MMP9, LGALS3, and OCLN for use in a method of diagnosing concussion or traumatic brain injury.

In any method and use described herein, 2, 3, or 4 biomarkers can be detected. For example, at least two biomarkers selected from the group consisting of copeptin, MMP9, LGALS3, and OCLN are detected (combinations include:
copeptin and MMP9;
copeptin and LGALS3;
copeptin and OCLN;
MMP9 and LGALS3;
MMP9 and OCLN; or
LGALS3 and OCLN).

For example, at least three biomarkers selected from the group consisting of copeptin, MMP9, LGALS3, and OCLN are detected for the methods (combinations include: copeptin, MMP9, and LGALS3; or copeptin, MMP9, OCLN; or MMP9, LGALS3, and OCLN).

For example, all four biomarkers are detected for the methods and uses described herein.

Biomarkers
Copeptin

Copeptin is a 39-amino acid peptide, which is a part of vasopressin prepro-hormone. Unlike vasopressin, this peptide is stable in plasma and is detected using ligands such as commercially available antibodies. In healthy individuals, the plasma levels of copeptin range between 1 and 12 pmol/L. Copeptin has been used as a diagnostic and prognostic marker for risk stratification in a variety of clinical situations, including myocardial infarction and heart failure, obstructive pulmonary disease, hemorrhagic and septic shock and stroke. In patients with severe TBI, the copeptin levels in plasma are significantly elevated and are strongly correlated with poor clinical outcome. In animals, vasopressin was found to play a critical role in the development and progression of secondary injury in severe TBI, consequently augmenting the loss of neural tissue. Plasma levels of copeptin in concussed patients were significantly lower than those observed in uninjured controls (FIG. 1A). These are the first data on copeptin obtained in patients sustaining mTBI.

The sequence of human copeptin provided below and is available on NCBI Accession No. NP_000481.2 GI:13259533.

(SEQ ID NO: 1)

```
  1  mpdtmlpacf lgllafssac yfqncprggk ramsdlelrq clpcgpggkg rcfgpsicca 61  delgcfvgta ealrcqeeny lpspcqsgqk acgsggrcaa fgvccndesc vtepecregf 121  hrrarasdrs natqldgpag alllrlvgla gapepfepaq pday
```

Exemplary regions or fragments of copeptin include residues 1-19 (signal peptide), residues 20-28; residues 32-124; residues 126-164; residues 39-116; and residues 20-164.

MMP9

MMP9 belongs to the family of enzymes involved in the breakdown of extracellular matrix. MMP9 has been considered a regulatory protein not only in wound repair and neovascularization, but also in neutrophil migration. This latter MMP9 action is most likely associated with the MMP9-mediated degradation of tight junction (TJ) proteins (e.g., OCLN). MMP9 activation is also associated with increased excitotoxicity, mitochondrial dysfunction, apoptosis, increased inflammatory response and astrogliosis. Selective inhibitors of MMP9 have been tested in several clinical trials unrelated to TBI, demonstrating their ability to reduce inflammation and infiltration of neutrophils and cytotoxic T-cells. The data described herein demonstrate an increase in plasma levels of MMP9 in concussed patients vs. uninjured control subjects (FIG. 1C), indicating that this protein represents a therapeutic target, mTBI.

The sequence of human MMP9 is provided below and available on NCBI Accession No. NP_004985.2 GI:74272287.

```
                                                            (SEQ ID NO: 2)
  1  mslwqplvlv llvlgccfaa prqrqstivl fpgdlrtnit drqlaeeyly rygytrvaem
 61  rgeskslgpa llllqkqlsl petgeldsat lkamrtprcg vpdlgrfqtf egdlkwhhhn
121  itywiqnyse dlpravidda farafalwsa vtpltftrvy srdadiviqf gvaehgdgyp
181  fdgkdgllah afppgpgiqg dahfdddelw slgkgvvvpt rfgnadgaac hfpfifegrs
241  ysacttdgrs dglpwcstta nydtddrfgf cpserlytqd gnadgkpcqf pfifqgqsys
301  acttdgrsdg yrwcattany drdklfgfcp tradstvmgg nsagelcvfp ftflgkeyst
361  ctsegrgdgr lwcattsnfd sdkkwgfcpd qgyslflvaa hefghalgld hssvpealmy
421  pmyrftegpp lhkddvngir hlygprpepe prppttttpq ptapptvcpt gpptvhpser
481  ptagptgpps agptgpptag pstattvpls pvddacnvni fdaiaeignq lylfkdgkyw
541  rfsegrgsrp qgpfliadkw palprkldsv feerlskklf ffsgrqvwvy tgasvlgprr
601  ldklglgadv aqvtgalrsg rgkmllfsgr rlwrfdvkaq mvdprsasev drmfpgvpld
661  thdvfqyrek ayfcqdrfyw rvssrselnq vdqvgyvtyd ilqcped
```

Exemplary regions or fragments of MMP9 include residues 1-19, residues 97-104, residues 107-707, residues 115-444, residues 224-271, residues 282-329, residues 341-388, residues 472-506, residues 514-704, residues 518-563, residues 564-608, residues 610-657, and residues 658-704.

LGALS3

LGALS3 is a β-galactoside-binding lectin. When compared with uninjured subjects, the plasma levels of LGALS3 in patients with mTBI are significantly increased (FIG. 1B). This observation indicates that similar to MMP9, LGALS3 represents a target for therapeutic intervention in mTBI.

The sequence of human LGALS3 is provided below and available on NCBI Accession No. CAG33178.1 GI:48145911.

Exemplary regions or fragments of LGALS3 include residues 18-105, and residues 117-244.

OCLN

OCLN is a transmembrane protein localized between endothelial cells and is involved in regulating the permeability of blood vessels. The brain blood vessels are known for their "tightness" and "impermeability" to blood-borne molecules. This distinct feature of brain blood vessels is called the blood-brain barrier (BBB) and is associated with the presence of TJs between adjacent brain endothelial cells. Changes in the permeability of the Blood Brain Barrier (BBB) have adverse effects on brain function. OCLN is a substrate for MMP9. Both in ischemia and in severe TBI or spinal cord injury, MMP9 degrades OCLN, disrupting TJ complexes and increasing the leakiness of the BBB. This process results in neuroinflammation and neuronal damage. The data described herein demonstrate an increase in plasma levels of OCLN in concussed patients vs. uninjured controls (FIG. 1D). These data also support the therapeutic targeting of OCLN in mTBI patients.

The sequence of human OCLN is provided below and available on NCBI Accession No. AAH29886.1 GI:20987418.

```
                                                            (SEQ ID NO: 3)
  1  madnfslhda lsgsgnpnpq gwpgawgnqp agaggypgas ypgaypgqap pgaypgqapp
 61  gaypgapgay pgapapgvyp gppsgpgayp ssggpsatga ypatgpygap agplivpynl
121  plpggvvprm litilgtvkp nanrialdfq rgndvafhfn prfnennrry ivcntkldnn
181  wgreergsvf pfesgkpfki qvlvepdhfk vavndahllq ynhrvkklne isklgisgdi
241  dltsasytmi
```

(SEQ ID NO: 4)
```
  1  mssrplespp pyrpdefkpn hyapsndiyg gemhvrpmls qpaysfyped eilhfykwts 61  ppgvirilsm liivmciaif acvastlawd rgygtsllgg svgypyggsg fgsygsgygy 121  gygygygygg ytdpraakgf mlamaafcfi aalvifvtsv irsemsrtrr yylsviivsa 181  ilgimvfiat ivyimgvnpt aqssgslygs qiyalcnqfy tpaatglyvd qysyhycvvd 241  pqeaiaivlg fmiivafali iffavktrrk mdrydksnil wdkehiydeq ppnveewvkn 301  vsagtqdvps ppsdyvervd spmayssngk vndkrfypes sykstpvpev vqelpltspv 361  ddfrqpryss ggnfetpskr apakgragrs krteqdhyet dyttggescd eleedwirey 421  ppitsdqqrq lykrnfdtgl qeykslqsel deinkelsrl dkelddyree seeymaaade 481  ynrlkqvkgs adykskknhc kqlksklshi kkmvgdydrq kt
```

Exemplary regions or fragments of OCLN include residues 55-521, residues 58-263, and residues 420-519.

Protein Release by Dying Brain Cells

Prior research on biomarkers for mTBI/concussion has been focused on proteins released by dying brain cells, such as neurons and glia. In principle, the blood levels of these proteins are expected to reflect the extent of cellular damage in the brain. Based on the data available in the literature, the following proteins have been considered as potential blood biomarkers for mTBI.

1) S100B—the peripheral sources of S100B have also been identified, raising the concern about its specificity for CNS injury. In addition, the commercially available essays frequently have low sensitivity, which makes it difficult to generate reproducible results.
2) Neuron-specific enolase-NSE-initially thought of as CNS-specific marker has been discovered to be produced by a variety of peripheral cells, including erythrocytes and platelets. This also indicates that the way the blood samples are collected and handled is critical to properly assess NSE levels.
3) Glial fibrillary acidic protein breakdown products GFAP-BP
4) Ubiquitin C-terminal hydrolase L1 UCHL1
5) Calpain-cleaved αII-spectrin N-terminal fragment SNTF
6) Total tau—it has recently been reported that the plasma levels of total tau could distinguish concussed patients from uninjured controls, though patients with OI were not included in this study.

GFAP-BP and UCHL1 appear to allow for differentiation between mTBI patients, uninjured controls, and the subjects with OI. Nevertheless, some overlap in serum concentrations of these biomarkers in mTBI and OI patients has been reported, raising concern about the claims of their high specificity for mTBI. The major weakness of these biomarkers is that their blood levels are very low, necessitating the employment of detection assays that are highly sensitive, complex, time-consuming, and costly. Therefore, these assays are unlikely to be easily implemented in emergency departments for routine diagnosis of mTBI. Furthermore, unlike our biomarkers, these proteins could not be targeted therapeutically.

Synthesis of Protein Following Brain Injury-Reliable Marker(s) for Identifying Concussion A unique combination of plasma biomarkers reliably diagnose concussion at an early time point after a potential brain injurious event, e.g., 1, 5, 10, 30, 50, 60 minutes; 1.5, 2, 5, 6, 8, 12, 24, 36, 48 hours; 1.5, 3, 5, 7, 10, 15, 30, 45, 60 days after a potential brain injurious event. Levels of proteins whose synthesis is altered as a consequence of concussion are measured. These biomarkers (copeptin, MMP9, LGALS3, OCLN) are readily detected using standard immunoassays, which are utilized for clinical use. In contrast, in traditional approach, the levels of proteins released by dying brain cells are measured in blood. Because of small neuronal damage associated with concussion/mTBI, the levels of these proteins in peripheral blood are exceedingly low and, therefore, difficult to measure. This represents one of the major obstacles for the implementation of these traditional biomarkers in clinical practice. Unlike proteins released by dying brain cells, markers identified by the data described herein represent targets for therapeutic intervention.

Because the plasma levels of these biomarkers are readily detectable with standard ELISA technique, rapid microfluidic immunoassays are suitable for point-of-care testing in emergency departments or other relevant environments.

Binding Agents for Biomarkers

Binding agents used in the methods described herein can be an antibody or a fragment thereof, a detectable protein or a fragment thereof or a nucleic acid molecule.

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM; preferably ≤100 nM and most preferably ≤10 nM.

Antibodies can be produced according to any method known in the art. For example, monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a full length protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (see pp. 59-103 in Goding (1986) Monoclonal Antibodies: Principles and Practice Academic Press). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In some examples the antibodies to an epitope for an interested protein as described herein or a fragment thereof are humanized antibodies. Humanized forms of non-human (e.g., murine) antibodies are chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al. 1986. Nature 321:522-525; Riechmann et al. 1988. Nature 332:323-329; Presta. 1992. Curr. Op. Struct. Biol. 2:593-596). Humanization can be essentially performed following methods of Winter and co-workers (see, e.g., Jones et al. 1986. Nature 321:522-525; Riechmann et al. 1988. Nature 332:323-327; and Verhoeyen et al. 1988. Science 239:1534-1536), by substituting rodent CDRs or CDR sequences for the corresponding sequences of a human antibody. Accordingly, such humanized antibodies are chimeric antibodies (e.g., U.S. Pat. No. 4,816,567), wherein substantially less than an intact human variable domain has been substituted by the corresponding sequence from a non-human species.

In another examples the antibodies to an epitope of an interested protein as described herein or a fragment thereof are human antibodies. Human antibodies can also be produced using various techniques known in the art, including phage display libraries (Hoogenboom and Winter. 1991. J. Mol. Biol. 227:381-388; Marks et al. 1991. J. Mol. Biol. 222:581-597) or the preparation of human monoclonal antibodies (e.g., Cole et al. 1985. Monoclonal Antibodies and Cancer Therapy Liss; Boerner et al. 1991. J. Immunol. 147(1):86-95). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in most respects, including gene rearrangement, assembly, and antibody repertoire. This approach is described, e.g., in U.S. Pat. Nos. 5,545,807; 5,545,806; 5,569,825; 5,625,126; 5,633,425; 5,661,016, and in the following scientific publications: Marks et al. 1992. Bio/Technology 10:779-783; Lonberg et al. 1994. Nature 368:856-859; Morrison. 1994. Nature 368: 812-13; Fishwild et al. 1996. Nature Biotechnology 14:845-51; Neuberger. 1996. Nature Biotechnology 14:826; Lonberg and Huszar. 1995. Intern. Rev. Immunol. 13:65-93. U.S. Pat. No. 6,719,971 also provides guidance to methods of generating humanized antibodies.

Exemplary antibodies against human copeptin protein include, but are not limited to, antibodies obtained from antibodies-online (e.g., Cat. No. ABIN109870, Cat. No. ABIN2238057, Cat. No. ABIN796775, and more can be found at its website www.antibodies-online.com), antibodies obtained from ThermoFisher Scientific (e.g., Cat. No. PA5-19788, Cat. No. PA5-25471; Cat. No. 710321, and more can be found at its website www.thermofisher.com), antibodies obtained from R&D systems (e.g., MAB6077), any commercially available antibodies against copeptin, and any antibodies that are generated by known method in the art utilizing the full-length protein or a fragment of human copeptin (e.g., residues 1-19, residues 20-28; residues 32-124; residues 126-164; residues 39-116; residues 20-164, any fragment or full length of SEQ ID NO 1).

Exemplary antibodies against human MMP9 protein include, but are not limited to, antibodies obtained from Novus Biologicals (e.g., MAB911, AF911, NBP1-57940, and more from novusbio.com), antibodies obtained from boster bio (e.g., PA1357, and more can be found at its website bosterbio.com), antibodies obtained from R&D systems (e.g., MAB911, AF911, and more from rndsystems.com), any commercially available antibodies against human MMP9, and any antibodies that are generated by known method in the art utilizing the full-length protein or a fragment of human MMP9 (e.g., residues 1-19, residues 97-104, residues 107-707, residues 115-444, residues 224-271, residues 282-329, residues 341-388, residues 472-506, residues 514-704, residues 518-563, residues 564-608, residues 610-657, residues 658-704, any fragment or full length of SEQ ID NO 2).

Exemplary antibodies against human LGALS3 protein include, but are not limited to, antibodies obtained from EMD Millipore (e.g., MABT51, MAB4033, AB10541, and more from emdmillipore.com), antibodies obtained from origene (e.g., TA506395, and more can be found at its website oregene.com), antibodies obtained from cell signaling technology (e.g., #12733, and more from rndsystems.com), any commercially available antibodies against human LGALS3, and any antibodies that are generated by known method in the art utilizing the full-length protein or a fragment of human LGALS3 (e.g., residues 18-105, residues 117-244, any fragment or full length of SEQ ID NO 3).

Exemplary antibodies against human OCLN protein include, but are not limited to, antibodies obtained from antibodies online (e.g., ABIN687337, ABIN657822, ABIN337048 and more from antibodies-online.com), antibodies obtained from Sigma (e.g., SAB1406198, and more can be found at its website sigmaaldrich.com), antibodies obtained from Thermo Scientific (e.g., PA5-20755, and more from pierce-antibodies.com), any commercially available antibodies against human OCLN, and any antibodies that are generated by known method in the art utilizing the full-length protein or a fragment of human OCLN (e.g., residues 55-521, residues 58-263, residues 420-519, any fragment or full length of SEQ ID NO 4).

Therapeutic Applications

Also provided herein is a method of treating concussion or traumatic brain injury by modulating the activity or level of a protein selected from the group consisting of copeptin, MMP9, LGALS3, and OCLN.

For example, the method includes steps of (1) providing a test sample from a subject, where the sample includes a bodily fluid; (2) performing a reaction in vitro by contacting the test sample with a binding agent to yield a complex including the binding agent and a protein selected from the group consisting of copeptin, MMP9, LGALS3, and OCLN; (3) detecting the complex, where a decrease in the level of the complex including copeptin compared to a normal control and an increase in the level of the complex including MMP9, LGALS3, or OCLN compared to a normal control indicates concussion or traumatic brain injury in the subject; and (4) administering to the subject identified as having concussion or traumatic brain injury a therapeutically effective amount of a compound that modulates the activity or level of the complex (e.g., an MMP9 selective inhibitor or an LGALS3 selective inhibitor), thereby treating the subject.

In some cases, the method includes administrating to a subject having concussion or mTBI a therapeutically effective amount of an MMP9 selective inhibitor and/or an LGALS3 selective inhibitor.

One exemplary MMP9 inhibitor is 2-[[(4-phenoxyphenyl)sulfonyl]methyl]-Thiirane (SB-3CT), SB-3CT prodrug or its pharmaceutically acceptable salt, ester, prodrug, metabolite, polymorph or solvate thereof (e.g., p-OH SB-3CT).

The structure of SB-3CT is:

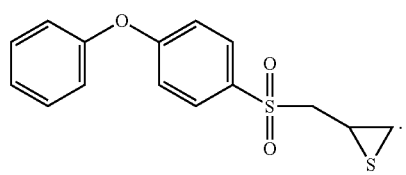 [SMILES: O=S(=O)(CC1CS1)c1ccc(Oc2ccccc2)cc1]

The structure of SB-3CT prodrug is:

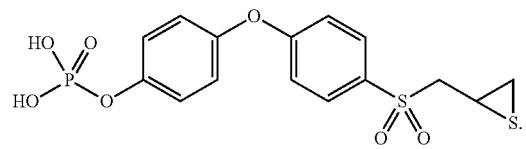 [SMILES: O=P(O)(O)Oc1ccc(Oc2ccc(S(=O)(=O)CC3CS3)cc2)cc1]

SB-3CT prodrug is metabolized primarily by hydroxylation at the para position of the terminal phenyl ring (p-OH SB-3CT) and this derivative is a more potent gelatinase inhibitor compared with the parent compound, having the following structure:

17

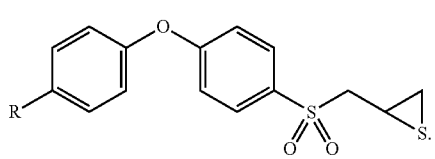

1: R = H
2: R = OH

Exemplary LGALS3 selective inhibitors include, but are not limited to, N-acetyllactosamine, a glycomimetic compound, or a pharmaceutically acceptable salt, ester, prodrug, metabolite, polymorph or solvate thereof.

18

N-acetyllactosamine has the following structure:

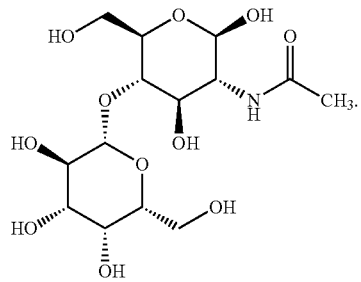 [SMILES: CC(=O)N[C@@H]1[C@@H](O)[C@H](O[C@@H]2O[C@H](CO)[C@H](O)[C@H](O)[C@H]2O)[C@@H](CO)O[C@H]1O]

Exemplary N-acetyllactosamine derivatives include, but are not limited to, the following compounds:

| glycomimetic compound | Structure |
|---|---|
| 1 | 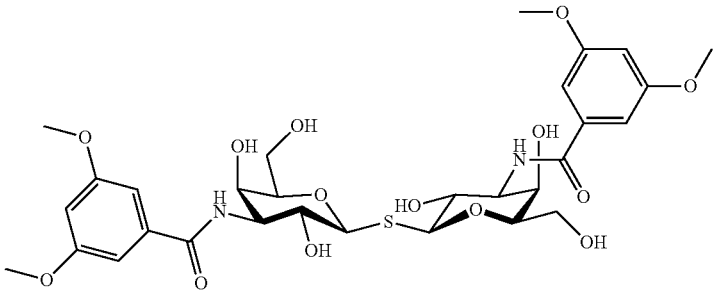 |
| 2 | 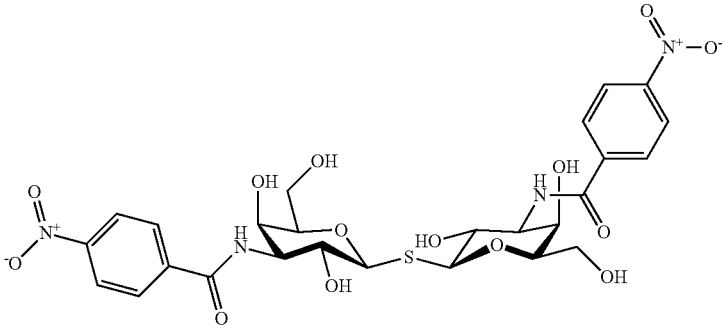 |
| 3 | 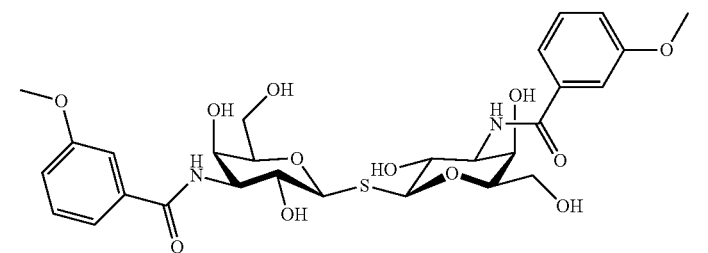 |
| 4 | 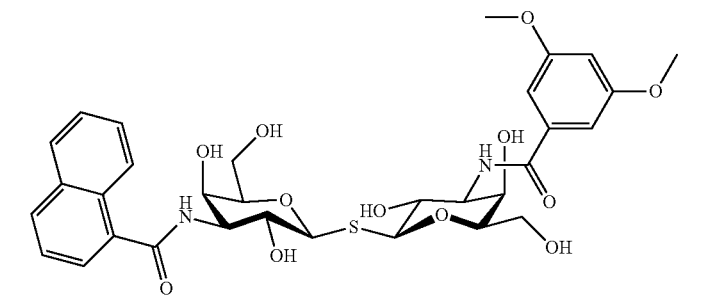 |

| glycomimetic compound | Structure |
|---|---|
| 5 | 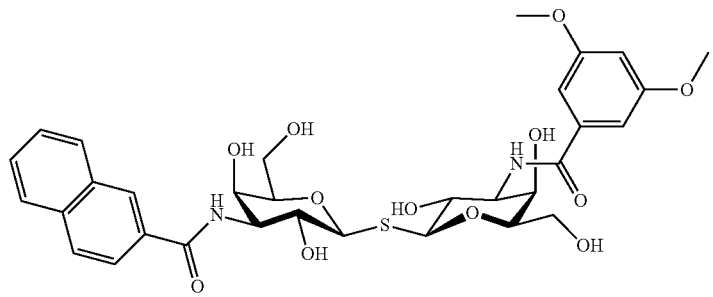 |
| 6 | 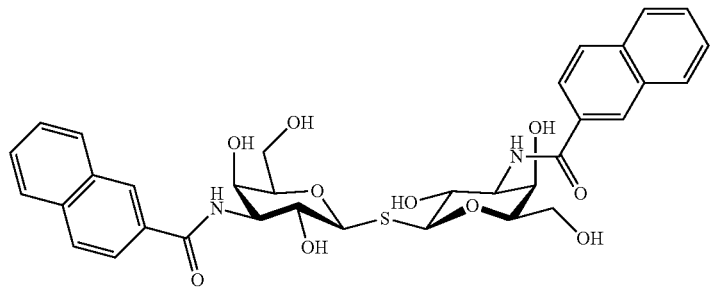 |
| 7 | 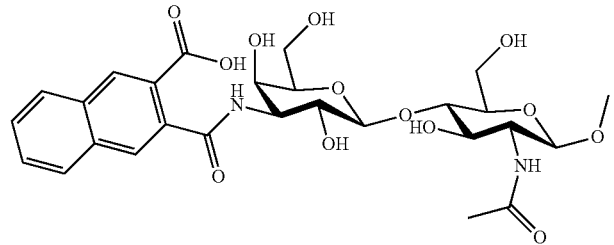 |
| 8 | 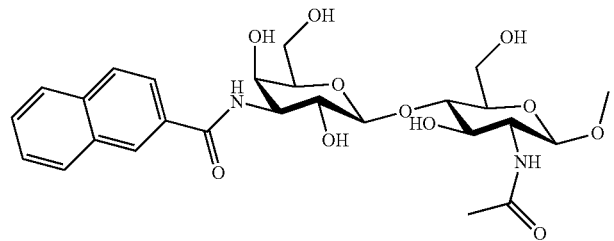 |
| 9 | 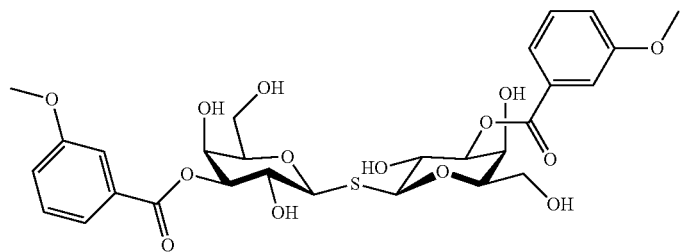 |

| glycomimetic compound | Structure |
|---|---|
| 10 | 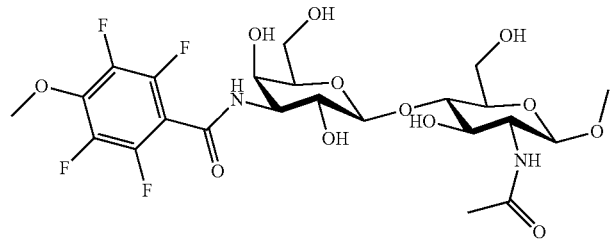 |
| 11 | 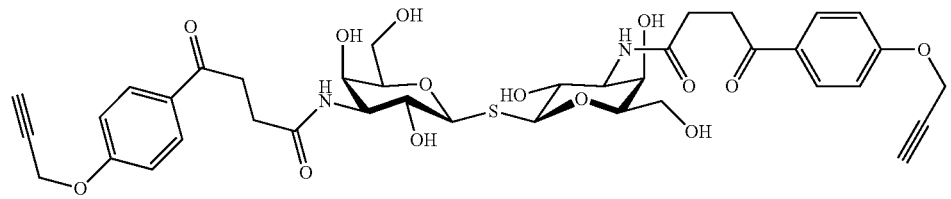 |
| 12 | 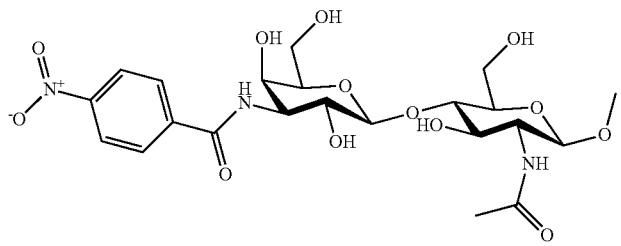 |
| 13 | 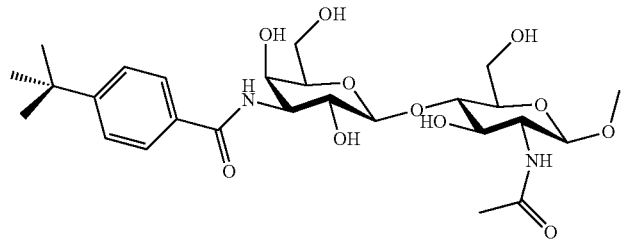 |
| 14 | 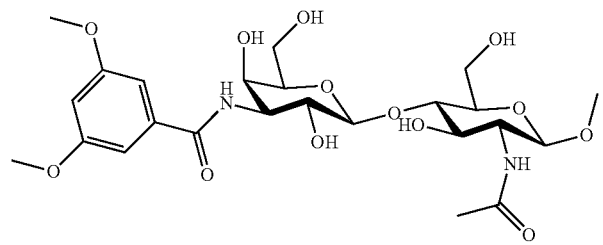 |
| 15 | 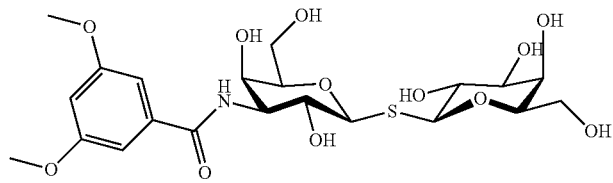 |

| glycomimetic compound | Structure |
|---|---|
| 16 | 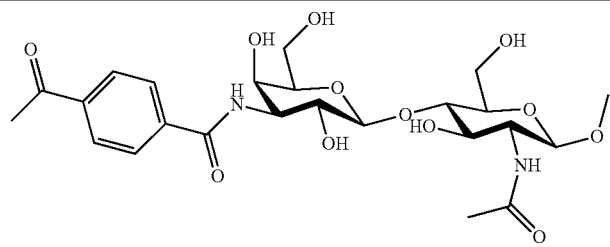 |
| 17 | 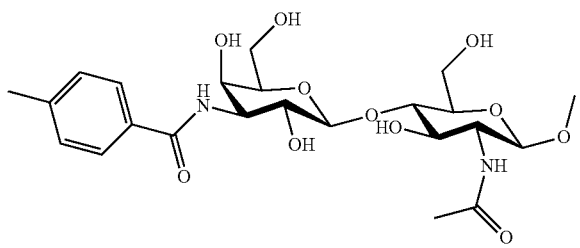 |
Exemplary N-acetyllactosamine derivatives include, but are not limited to, the following compounds:
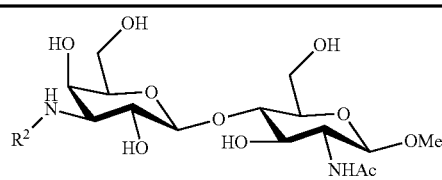
12-23
| Compound 12-23 | R² = |
|---|---|
| 12 | H |
| 13 | Ac |
| 14 | 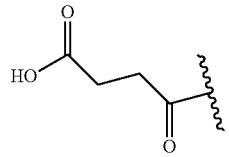 [SMILES: *C(=O)CCC(=O)O] |
| 15 | 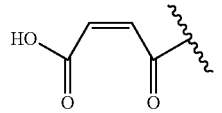 [SMILES: *C(=O)/C=C\C(=O)O] |
| 16 | 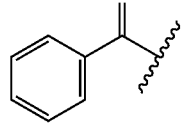 |
| 17 | 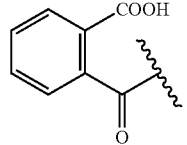 [SMILES: *C(=O)c1ccccc1C(=O)O] |
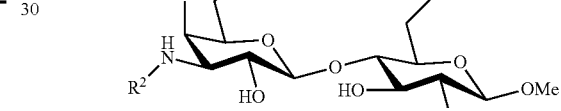
12-23
| Compound 12-23 | R² = |
|---|---|
| 18 | 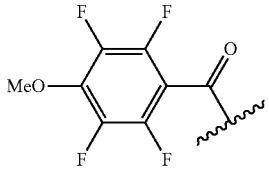 [SMILES: *C(=O)c1c(F)c(F)c(OC)c(F)c1F] |
| 19 | CH₃SO₂ |
| 20 | 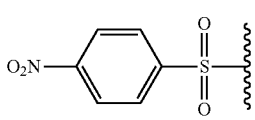 |
| 21 | 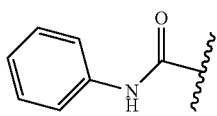 |
| 22 | 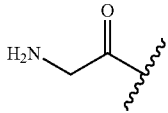 |

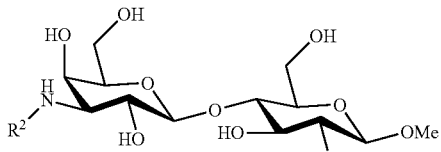

12-23

Compound 12-23    R² =

23
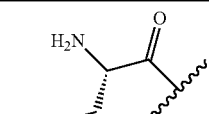

24
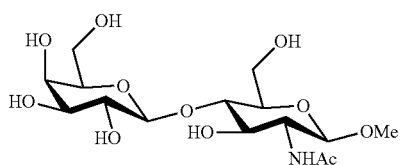

The term "therapeutically effective amount", as used herein, refers to an amount of a pharmaceutical agent to treat or ameliorate an identified disease or condition (i.e., concussion/mTBI), or to exhibit a detectable therapeutic or inhibitory effect, such as alleviation or amelioration of symptoms (e.g., amnesia, nausea, vomiting, headache, diplopia, dizziness, sleepiness, confusion, and/or disorientation/sensation of "fogginess"). The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician.

The invention here also provides a method of treating concussion or traumatic brain injury by administering an inhibitor of MMP9 and/or an inhibitor of LGALS3. In some embodiments, the method does not comprise administering an inhibitor of copeptin or OCLN.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years).

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, N.Y.-Oxford (1985).

Diagnostic Device

Also provided herein is diagnostic device that includes a solid support and a binding agent immobilized on the support, where the binding agent binds to a protein selected from the group consisting of copeptin, MMP9, LGALS3, and OCLN.

In some cases, the diagnostic device includes a solid support and a plurality of immobilized binding agents, where a first binding agent binds to copeptin, a second binding agent binds to MMP9, a third binding agent binds to LGALS3, or a fourth binding agent binds to OCLN. A standard assay format for detection of these proteins in plasma or other processed bodily fluids includes ELISA or miniaturized ELISA-format system, e.g, on a chip. In some cases, the device is in a format/size of a credit card. In some cases, a diagnosis result (e.g., color change indicative of the change, presence and/or level of antigen (biomarker) present in the patient sample) is read, detected and/or sent to a second device, such as smart phone.

An enzyme-linked immunosorbent assay (ELISA) is a test that uses antibodies and color change to identify the presence of an antibody-antigen complex. In this case, the antigen to be identified and quantified is a biomarker of concussion as described above. ELISA is an analytic biochemistry assay that uses a solid-phase enzyme immunoassay (EIA) to detect the presence of a substance, usually an antigen, in a liquid sample or wet sample. There are multiple forms of ELISA: direct ELISA, "sandwich" ELISA, and competitive ELISA.

The steps of direct ELISA follows the mechanism: (1) a buffered solution of the antigen to be tested for is added to each well of a microtiter plate, where it is given time to adhere to the plastic through charge interactions; (2) a solution of nonreacting protein, such as bovine serum albumin or casein, is added to well (usually 96-well plates) in order to cover any plastic surface in the well which remains uncoated by the antigen; (3) the primary antibody with an attached (conjugated) enzyme is added, which binds specifically to the test antigen coating the well; (4) a substrate for this enzyme is then added. Often, this substrate changes color upon reaction with the enzyme. The higher the concentration of the primary antibody present in the serum, the stronger the color change. Often, a spectrometer is used to give quantitative values for color strength.

The enzyme acts as an amplifier; even if only few enzyme-linked antibodies remain bound, the enzyme molecules will produce many signal molecules. The enzyme can go on producing color indefinitely, but the more antibody is bound, the faster the color will develop. A major disadvantage of the direct ELISA is the method of antigen immobilization is not specific; when serum is used as the source of test antigen, all proteins in the sample may stick to the microtiter plate well, so small concentrations of analyte in serum must compete with other serum proteins when binding to the well surface. The sandwich or indirect ELISA provides a solution to this problem, by using a "capture" antibody specific for the test antigen to pull it out of the serum's molecular mixture.

ELISA may be run in a qualitative or quantitative format. Qualitative results provide a simple positive or negative result (yes or no) for a sample. The cutoff between positive and negative is determined by the analyst and may be statistical. Two or three times the standard deviation (error inherent in a test) is often used to distinguish positive from negative samples. In quantitative ELISA, the optical density (OD) of the sample is compared to a standard curve, which is typically a serial dilution of a known-concentration solution of the target molecule. For example, if a test sample returns an OD of 1.0, the point on the standard curve that gave OD=1.0 must be of the same analyte concentration as the sample.

The use and meaning of the names "direct ELISA" and "indirect ELISA" differs in the literature depending on the context of the experiment. When the presence of an antigen is analyzed, the name "direct ELISA" refers to an ELISA in which only a labelled primary antibody is used, and the term "indirect ELISA" refers to an ELISA in which the antigen is bound by the primary antibody which then is detected by a labelled secondary antibody. In the latter case a sandwich ELISA is clearly distinct from an indirect ELISA. When the 'primary' antibody is of interest, e.g. in the case of immunization analyses, this antibody is directly detected by the secondary antibody and the term "direct ELISA" applies to a setting with two antibodies.

A "sandwich" ELISA, is used to detect sample antigen. The steps are: (1) a surface is prepared to which a known quantity of capture antibody is bound; (2) any nonspecific binding sites on the surface are blocked; (3) the antigen-containing sample is applied to the plate, and captured by antibody; (4) the plate is washed to remove unbound antigen; (5) a specific antibody is added, and binds to antigen (hence the 'sandwich': the Ag is stuck between two antibodies). This primary antibody could also be in the serum of a donor to be tested for reactivity towards the antigen; (6) enzyme-linked secondary antibodies are applied as detection antibodies that also bind specifically to the antibody's Fc region (nonspecific); (7) the plate is washed to remove the unbound antibody-enzyme conjugates; (8) a chemical is added to be converted by the enzyme into a color or fluorescent or electrochemical signal; (9) the absorbance or fluorescence or electrochemical signal (e.g., current) of the plate wells is measured to determine the presence and quantity of antigen.

In some cases, a secondary antibody is conjugated to an enzyme, although, in the technical sense, this is not necessary if the primary antibody is conjugated to an enzyme (which would be direct ELISA). However, the use of a secondary-antibody conjugate avoids the expensive process of creating enzyme-linked antibodies for every antigen one might want to detect. By using an enzyme-linked antibody that binds the Fc region of other antibodies, this same enzyme-linked antibody can be used in a variety of situations. Without the first layer of "capture" antibody, any proteins in the sample (including serum proteins) may competitively adsorb to the plate surface, lowering the quantity of antigen immobilized. Use of the purified specific antibody to attach the antigen to the plastic eliminates a need to purify the antigen from complicated mixtures before the measurement, simplifying the assay, and increasing the specificity and the sensitivity of the assay.

A third use of ELISA is through competitive binding. The steps for this ELISA are somewhat different from the first two examples: (1) unlabeled antibody is incubated in the presence of its antigen (sample); (2) these bound antibody/antigen complexes are then added to an antigen-coated well; (3) the plate is washed, so unbound antibodies are removed. (The more antigen in the sample, the more Ag-Ab complexes are formed and so there are less unbound antibodies available to bind to the antigen in the well, hence "competition".); (4) the secondary antibody, specific to the primary antibody, is added (this second antibody is coupled to the enzyme); (5) a substrate is added, and remaining enzymes elicit a chromogenic or fluorescent signal; (6) the reaction is stopped to prevent eventual saturation of the signal.

Some competitive ELISA kits include enzyme-linked antigen rather than enzyme-linked antibody. The labeled antigen competes for primary antibody binding sites with the sample antigen (unlabeled). The less antigen in the sample, the more labeled antigen is retained in the well and the stronger the signal. Commonly, the antigen is not first positioned in the well.

The support can be a strip, a glass, a silicon, a polymer, a bead, a nanoparticle or a chip (e.g., microfluidics). In some cases, the support comprises a microfluidic system. Microfluidic systems fabricated by microelectromechanical systems (MEMS) technology are now usually referred to as"lab-on-a-chip" (LOC), "biochips," or"micro-total-analysis-system." They are fabricated as miniaturized versions of their large-scale counterparts. These miniaturized systems can carry out entire protocols traditionally performed in a laboratory. Sample pretreatment, sample/reagent transport, mixing, reaction, separation, detection, and product collection can all be performed automatically on a single LOC system. Functional microfluidic devices, such as micropumps, microvalves, microfilters, microreactors, and microseparators can be microfabricated and even integrated to perform a specific assay. The advantages of these developed LOC systems include less sample/reagent consumption, a reduced risk of contamination, enhanced sensitivity, less unit cost, lower power consumption, and a higher reliability and functionality. More importantly, portability arising from their compact form is a key factor for point-of-care (POC) applications.

Microfluidic devices for immunoassays can be fabricated from a variety of materials. The most commonly used substrate materials are silicon, glass, and polymers. Many polymers have been used in microfluidic applications, such as polymethyl methacrylate (PMMA), polycarbonate, polystyrene (PS), and polydimethylsiloxane (PDMS). Among these polymers, PDMS is one of the most commonly used materials for microfluidic immunoassays in recent studies because of its desirable characteristics, such as flexibility, optical transparency (down to 230 nm), and biocompatibility. Heterogeneous materials formed by using two different types of materials can also be utilized for microfluidic devices. For example, PDMS/glass and silicon/glass are commonly used for forming microfluidic devices.

Such device is portable and convenient, and provides a quick (e.g., between about 10-40 min, e.g., about 10, 20, 30, 40 minutes) and accurate diagnosis result for the patients. In addition, only a small volume from about 10 µl to about 200 µl (e.g., about 10, 20, 30, 40, 50, 60, 70, 80, 90, 100, 110, 120, 130, 140, 150, 160, 170, 180, 190, or 200 µl) of blood sample is sufficient for an accurate determination.

Any binding agent that binds to copeptin, MMP9, LGALS3 or OCLN can be used in the devices described herein, for example, an antibody or a fragment thereof, a detectable protein or a fragment thereof. The antibody can be a polyclonal antibody or a monoclonal antibody. Exemplary antibodies are described above. Other exemplary binding agents that can be used in the device include, but are not limited to, DuoSet ELISA Development Systems from R&D Systems (Minneapolis, Minn.) for LGALS3 and MMP9 and the ELISA kits from USCN Life Science for OCLN and copeptin.

In some cases, the antibody is conjugated to a detectable moiety. Exemplary detectable moiety includes, but is not limited to a fluorescent marker (e.g., fluorescein isothiocyanate, rhodamine, phycoerythrin, phycocyanin, allophycocyanin, p-phthaldehyde and fluorescamine, and 152 Eu) or a chemiluminescent compound (e.g., luminol, isoluminol, theromatic acridinium ester, imidazole, acridinium salt and oxalate ester).

Exemplary Study: A Panel of Blood Biomarkers for Diagnosis of Mild Traumatic Brain Injury/Concussion No routine tests currently exist to objectively diagnose mild traumatic brain injury mTBI/concussion with high level of accuracy and confidence. The methods and systems described herein solve this problem and provide a rapid and reliable test for concussion. Previously reported biomarkers for mTBI represented proteins released from the damaged neurons or glia. However, the low levels of these proteins and/or the complexity of assays used for their detection limits the implementation of these biomarkers in routine practice. Proteins whose synthesis is altered after mTBI and whose blood levels are accordingly measured using standard immunoassays were identified.

Adult patients sustaining a concussion within the past 24 hours were enrolled in the study. Controls were uninjured subjects and patients with orthopedic injury (04 Plasma concentrations of eighteen potential biomarkers were measured using commercially available immunoassays.

Four biomarkers were identified: copeptin, galectin 3 (LGALS3), matrix metalloproteinase 9 (MMP9), and occludin (OCLN). A 3.4-fold decrease in plasma concentration of copeptin was found in mTBI patients within eight hours after accident when compared to uninjured controls. Plasma levels of LGALS3, MMP9, and OCLN increased 3.6-4.5-fold within the same time frame post-injury. The levels of at least two biomarkers were altered beyond their respective cutoff values in 90% of mTBI patients, whereas in none of uninjured controls, were the levels of two biomarkers simultaneously changed. A positive correlation between the plasma levels of LGALS3 and OCLN was also found in mTBI patients, whereas in OI patients or uninjured subjects, these variables did not correlate.

This panel of biomarkers discerns with high accuracy concussed patients from uninjured individuals within the first eight hours after accident. Furthermore, these biomarkers are useful to diagnose concussion in the presence of OI. Unlike the previously reported biomarkers, some of these proteins represent potential therapeutic targets in mTBI.

In the present study, an alternative approach was explored. Proteins whose synthesis are upregulated in response to mTBI were identified, resulting in an increase in their blood levels, which could be readily measured using standard, immunoassays. In contrast to the above-described biomarkers, these proteins also represent potential targets for intervention.

The following methods were used to generate the data described herein.

Study Design and Participants

This study was conducted in a large, urban academic ED with a level I trauma center. Research subjects were selected by research assistants (RAs) based upon electronic medical record review of the chief complaint and initial triage nursing notes. RAs, who were trained in recognizing the signs and symptoms of concussion, performed a brief interview with the subjects to determine eligibility. The definition and inclusion criteria for concussion were based on the 2012 Zurich Concussion Consensus Statement. If subjects were eligible, RAs collected demographic and clinical information, and then obtained blood samples through venipuncture. Control OI subjects with long bone fractures were recruited in the same ED. The same exclusion criteria applied to these subjects with the exception of the presence of long bone fractures and the absence of mTBI within the past six months. Control uninjured subjects were recruited by research staff. These subjects were not patients in the ED. The same exclusion criteria were applied to this group of subjects with the addition of no mTBI within the past six months.

Biochemical Procedures

The recommendations from the Biospecimens and Biomarkers Working Group[19] were followed when collecting and processing blood samples. Blood was collected using heparin-containing Va-cutainer tubes. Plasma was subsequently isolated, aliquoted, and stored at −80° C. Plasma rather than serum was analyzed in this study because of our concern that the coagulation process may have an effect on the concentration of some of the biomarkers. This was based on our data obtained in the rat model of mTBI where the serum levels of chemokine (C—X—C motif) ligand 1 (CXCL1) were substantially higher than those measured in plasma. Additionally, unlike plasma levels of CXCL1, serum levels of CXCL1 did not change in response to injury.

Eighteen potential biomarkers were studied. These proteins included proinflammatory mediators tumor necrosis factor alpha (TNF-a) and its soluble receptor, sTNFR1 (samples diluted 1:5), interleukin-1b (IL-1b), the chemokines CXCL1, CXCL8, and chemokine (C—C motif) ligand 2 (CCL2), colony-stimulating factor 3 (CSF3), SPP1 (samples diluted 1:200), LGALS3 (samples diluted 1:5), soluble cell adhesion molecules intercellular adhesion molecule 1 (sICAM1; samples diluted 1:200), sE-selectin (samples diluted 1:20), sP-selectin (samples diluted 1:20), and sL-selectin (samples diluted 1:1000), matrix metalloproteinases MMP2 (samples diluted 1:50), MMP3 (samples diluted 1:100), and MMP9 (samples diluted 1:100), occludin (OCLN), and copeptin. Plasma concentrations of these proteins were measured using commercially available enzyme-linked immunosorbent assay (ELISA) kits with appropriate dilutions of the samples (as indicated above) to adjust for the assay range for each ELISA. DuoSet ELISA Development Systems from R&D Systems (Minneapolis, Minn.) were used to measure the concentrations of all biomarkers except for OCLN and copeptin. Levels of OCLN and copeptin were measured using the ELISA kits from USCN Life Science (Houston, Tex.).

Statistical Analysis

For statistical analysis, plasma concentrations of candidate biomarkers were considered as continuous data. Results are expressed as means—standard deviation. In addition, a median and interquartile range (IQR) of concentrations for each biomarker were provided. Kruskal-Wallis' one-way analysis of variance was used followed by Dunn's test to compare mTBI patients with uninjured control subjects and patients with OI. Effect sizes (Cohen's d) for changes in plasma levels of four candidate biomarkers were also assessed. A pair-wise analysis of correlation for these biomarkers was also performed and Pearson's correlation coefficients were calculated. To determine whether the candidate biomarkers have the ability to discriminate between patients with mTBI and uninjured control subjects, receiver operating characteristics (ROC) curves were generated and the area under the curve (AUC), together with its 95% confidence interval (CI), was estimated for each ROC curve. Both uni- and multivariate ROC analyses were performed to evaluate the diagnostic performance of individual biomarkers and their combinations, respectively.

In addition, a multivariate logistic regression analysis, controlling for age, sex, and body mass index (BMI), was performed to assess odds ratios (ORs) for the ability of candidate biomarkers to diagnose suspected concussion. A value of $p<0.05$ was considered statistically significant. Statistical analyses were performed using the statistical software packages, GraphPad Prism (version 6.0; GraphPad Software Inc., La Jolla, Calif.) and SigmaStat (version 12.5; Systat Software, Inc., San Jose, Calif.). Effect sizes (Cohen's d) were calculated using the Psychometrica online tool (http://www.psychometrica.de/effect_size.html), whereas the uni- and multivariate ROC analyses were performed using ROCCET, an online tool for ROC analysis (www.roccet.ca/ROCCET/).

Identification of Biomarkers

In total, 55 patients sustaining a concussion were enrolled. We also enrolled 44 uninjured control subjects and 17 subjects with long bone fractures who constituted the OI group. The characteristics of enrolled subjects, including their demographic data, the mechanisms of injury, and medical history, are provided in Table 2. The initial goal was to investigate whether concussion in humans is accompanied by increased production of proinflammatory mediators, as they potentially represent targets for therapeutic intervention. A group of mTBI patients were divided into two subgroups. The first subgroup—mTBI (1-8 h)—which represented the majority (41 or 75%) of participants, included mTBI patients in whom blood samples were collected within the first eight hours after concussion. The second subgroup—mTBI (9-24 h)—consisted of mTBI patients in whom blood samples were collected between nine and twenty-four hours after accident. The earliest time point at which blood was drawn in the mTBI (1-8 h) subgroup of patients was 1.5 h after injury, and the mean time between injury and blood collection was 4.2±1.6 h (median 4 h, IQR 3-5 h). In the mTBI (9-24 h) subgroup of patients, the mean period of time between injury and the collection of blood sample was 15.5±5.4 h (median 13 h, IQR 10.4-22.0 h). In OI patients, the blood samples were collected within 12 h after accident, with a mean of 6.6±3.2 h (median 6 h, IQR 3.5-9.0 h).

Overall, 18 potential biomarkers were evaluated. For 14 of these proteins, no differences in their plasma levels were found between the mTBI (1-8 h) subgroup of patients and uninjured control subjects (Table 3). A considerable dispersion of plasma concentrations of tumor necrosis factor-α and interleukin-1β, and the chemokines CXCL1, CXCL8, and CCL2, was observed in both groups. This could be related, at least in part, to the existence of various underlying medical conditions in some of the participating individuals (see Table 2).

Data obtained in two rodent models of severe TBI indicated that the brain synthesis of two proinflammatory mediators osteopontin (SPP1) and galectin 3 (LGALS3) is rapidly upregulated and maintained at high levels for at least three days after injury. While the plasma level of SPP1 did not change after mTBI (Table 3), a 4.3-fold increase in plasma concentration of GALS3 was found in the mTBI (1-8 h) subgroup of patients when compared to controls (FIGS. 1A-1D). Plasma level of GALS3 in the mTBI (9-24 h) subgroup of patients was not different from that found in uninjured subjects.

Changes in plasma levels of select MMPs were also evaluated in mTBI patients. No changes in plasma levels of MMP2 and MMP3 were found in the mTBI (1-8 h) subgroup of patients compared to uninjured controls (Table 3); however, a 3.6-fold increase in plasma concentration of MMP9 was observed in the mTBI (1-8 h) subgroup of patients versus controls (FIGS. 1A-1D). A smaller (1.9-fold) increase in MMP9 concentration was maintained for at least 24 h after injury. MMP9 is well known for its ability to disrupt the integrity of the blood-brain barrier (BBB) by attacking basal lamina proteins and degrading the components of the tight junction complexes. Accordingly, whether mTBI is associated with increased plasma levels of degradation products of tight junction protein occludin (OCLN), a substrate for MMP9, was examined. As shown in FIGS. 1A-D, a 4.5-fold increase in plasma concentration of OCLN was observed in the mTBI (1-8 h) subgroup of patients compared to uninjured controls. The post-traumatic production of MMP9 is regulated by vasopressin, a neuropeptide whose synthesis is augmented after injury not only in the hypothalamic magnocellular neurons, but also in macrophages/microglia located in the injured brain parenchyma. Therefore, whether the plasma concentration of copeptin (a stable C-terminal fragment of preprovasopressin) is elevated in mTBI was also tested. Surprisingly, a 3.4-fold decrease in plasma concentration of copeptin was found in the mTBI (1-8 h) subgroup of patients compared to uninjured controls (FIGS. 1A-1D). Importantly, this decrease in copeptin level was maintained for at least 24 h after injury.

Figure 2F:
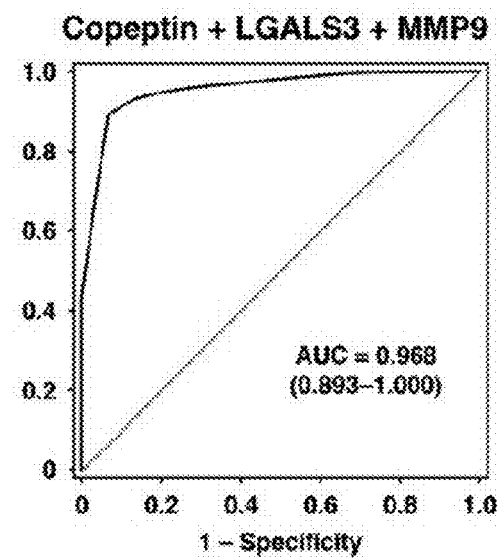

These investigations led to the identification of four biomarkers for the diagnosis of mTBI within eight hours after injury. The majority (23 out of 26 or 88%) of individuals in the mTBI (1-8 h) subgroup of patients in whom the Glasgow Coma Scale (GCS) scores were recorded had a GCS score of 15. None of these mTBI patients had a GCS score of 13. The diagnostic performance of these biomarkers is summarized in Table 3, and FIG. 2A-2F shows the ROC curves for each candidate biomarker, with the AUC values ranging between 0.836 and 0.922. The combination of three biomarkers (copeptin+LGALS3+MMP9) substantially improved sensitivity and specificity of the test, when compared with each biomarker analyzed separately (FIG. 2F). No further improvement in sensitivity and specificity was found when all four biomarkers were combined (AUC=0.964; CI=0.891-1.000). The plasma levels of at least two biomarkers were altered beyond their respective cutoff values (see Table 1) in 90% of individuals in the mTBI (1-8 h) subgroup of patients, whereas in none of uninjured controls, were the plasma levels of two biomarkers simultaneously changed. After controlling for age, sex, and BMI, the OR values for the ability of candidate biomarkers to diagnose suspected concussion ranged between 9.0 and 94.2 (Table 1).

TABLE 1

Diagnostic performance of biomarkers

| | Biomarker | | | |
|---|---|---|---|---|
| | Copeptin | LGALS3 | MMP9 | OCLN |
| Type of analysis | | | | |
| ROC analysis* | | | | |
| AUC | 0.922 | 0.849 | 0.846 | 0.836 |
| 95% CI | 0.855-0.989 | 0.763-0.935 | 0.759-0.933 | 0.746-0.926 |
| Statistical significance | p < 0.0001 | p < 0.0001 | p < 0.0001 | p < 0.0001 |
| Cutoff value | 375 pg/mL | 1 ng/mL | 30 ng/mL | 350 pg/mL |
| PPV | 94.6% | 71.4% | 90.6% | 87.5% |
| Sensitivity/specificity | 0.833/0.933 | 0.775/0.733 | 0.725/0.930 | 0.683/0.879 |
| Logistic regression analysis† | | | | |
| OR | 94.2 | 9.0 | 34.5 | 19.3 |
| 95% CI | 15.4-577.4 | 3.2-25.6 | 8.6-138.1 | 5.2-72.5 |
| Statistical significance | p < 0.001 | p < 0.001 | p < 0.001 | p < 0.001 |

ROC = receiver operating characteristics.
AUC = area under the curve.
CI = confidence interval.
PPV = positive predictive value.
OR = odds ratio.
*ROC analyses were conducted to assess the ability of biomarkers to discriminate between in TBI patients (blood samples collected at 1-8 h post injury) and uninjured subjects.
†Logistic regression analyses were adjusted for age, sex, and body mass index.

The above-described biomarkers are useful for the diagnosis of isolated concussions. The plasma levels of these biomarkers may also be altered in patients with OI (FIGS.

Figure 3:
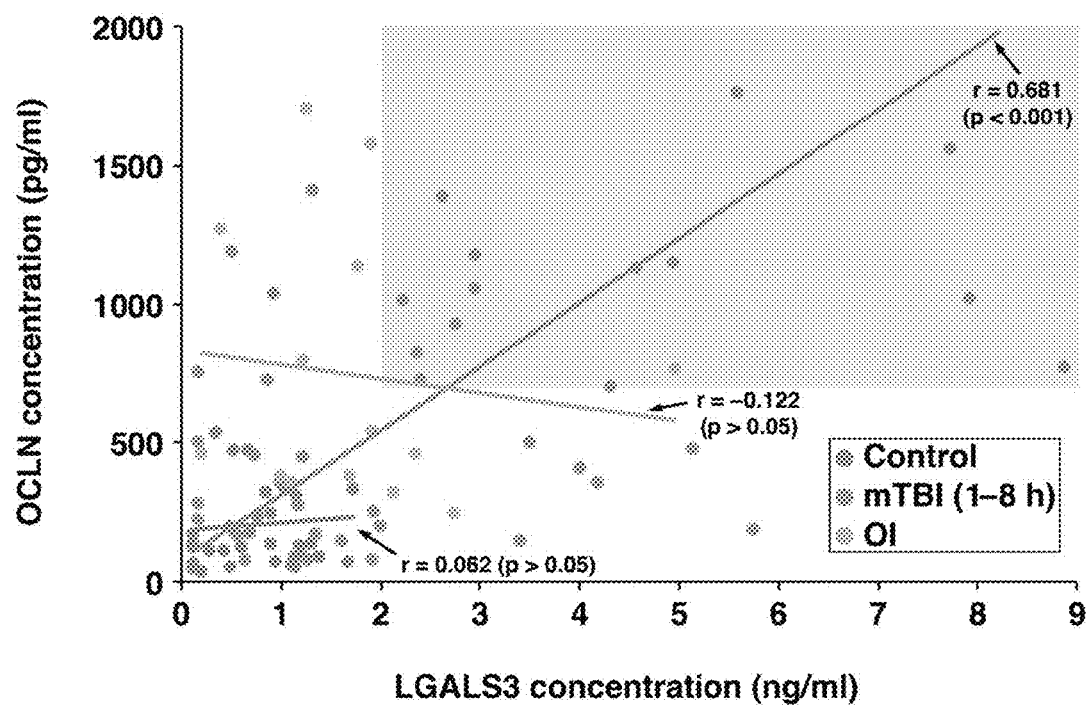
FIG. 3 is a graph showing the correlation between plasma concentrations of LGALS3 and OCLN. A positive correlation between plasma levels of LGALS3 and OCLN exists in the mTBI (1-8 h) subgroup of patients, whereas in uninjured control subjects and OI patients, these variables do not correlate. This can aid in diagnosing suspected concussion in the presence of OI. The shaded area represents the plasma concentrations of LGALS3 and OCLN that are higher than twice their respective cutoff values (determined based on ROC analyses; see table 1). Plasma concentrations of both LGALS3 and OCLN exceeded these levels in 15 out of 40 (38%) mTBI patients, but only in 1 out of 17 (7%) patients with OI. Control=uninjured subjects. mTBI (1-8 h)=mTBI patients in whom blood samples were collected between 1 and 8 h after injury. OI=subjects with orthopedic injury. r=Pearson's correlation coefficient.
Figure 4:
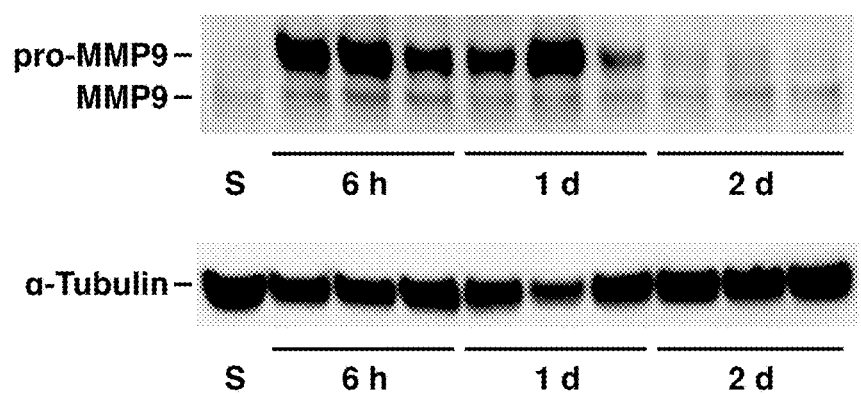
FIG. 4 is a western blot result showing MMP9 expression in the plasma in a rat model of mTBI. S indicates sham, whereas 6 h, 1 d, and 2 d indicate time points post-mTBI.

1A-1D). Further analysis of the data demonstrated that in the mTBI (1-8 h) subgroup of patients, there is a positive correlation between the plasma levels of LGALS3 and OCLN (Pearson's correlation coefficient r=0.681, p<0.001), whereas in OI patients or uninjured control subjects, these variables did not correlate (FIG. 3). This could help in diagnosing concussion in the presence of OI. Indeed, it was found that in 15 out of 40 (38%) individuals in the mTBI (1-8 h) subgroup of patients, the plasma concentrations of both LGALS3 and OCLN were higher than twice their respective cutoff values (the shaded area in FIG. 3), whereas in only 1 out of 17 (7%) subjects with OI, did the plasma concentrations of LGALS3 and OCLN exceed these levels.

In the course of these studies, a panel of four biomarkers for mTBI was defined. These markers accurately and reliably discern with high accuracy patients sustaining a concussion from uninjured subjects within the first eight hours after injury. These biomarkers can also aid in diagnosing suspected concussion in the presence of OI. The AUC values for these biomarkers are comparable to those reported for GFAP breakdown products, UCHL1, total tau, and S100B. The ability of these biomarkers to diagnose mTBI is not influenced by age, sex, or BMI. Since many individuals among mTBI patients and control subjects suffered from various diseases and/or were on various medications (Table 2). The diagnostic performance of these biomarkers is also independent of underlying medical conditions or medications taken by a patient. The plasma levels of these biomarkers can be altered by OI; however, this phenomenon is not unique to these proteins. Indeed, among apparently CNS-derived biomarkers investigated so far, UCHL1 appears to be the only biomarker that could potentially distinguish patients with mTBI from those with OI. While such data are not available for total tau, a noticeable overlap in serum levels of GFAP breakdown products between the mTBI and OI groups of patients, with comparable median values, was found. Similarly, no difference in serum levels of S100B between mTBI and OI patients was observed, and in a study assessing the diagnostic potential of SPTAN1 N-terminal fragment, the plasma levels of this protein were found to be elevated above an arbitrary cutoff value in 23% of OI subjects. These observations could be explained, at least in part, by findings demonstrating that long bone fractures cause the disruption of the integrity of the BBB and neuroinflammation.

Copeptin was found to be the best performing biomarker for mTBI. Its plasma concentration was not only significantly decreased early after concussion, but was also maintained at the low level for at least 24 h post-mTBI. These observations are surprising given previous data obtained in a rat model of severe TBI and the results of clinical studies of patients with severe TBI, demonstrating an increase in vasopressin synthesis. The reasons for these apparent discrepancies are currently unknown and may be related to the reduced synthesis/secretion and/or augmented degradation of circulating copeptin in mTBI patients. This also suggests that the pathophysiology of TBI in humans is not a continuum between mTBI and severe TBI.

MMP9 has never been evaluated as a potential biomarker for mTBI. With a significant (3.6-fold) increase in MMP9 concentration in plasma observed in mTBI patients versus uninjured controls, and a well-established ability of this proteinase to attack tight junction proteins at the BBB, whether this increase in MMP9 level is accompanied by an increase in the concentration of OCLN was investigated. While a rise in OCLN levels within eight hours after concussion was also observed, no correlation between plasma concentrations of MMP9 and OCLN was found, suggesting that MMP9 is not involved in OCLN degradation occurring after mTBI. At present, it is unclear whether this increase in OCLN concentration reflects dysfunction of the BBB in patients with mTBI. No change in albumin levels in cerebrospinal fluid (CSF) harvested from boxers sustaining concussions (based on the measurements of CSF levels of neurofilament light chain protein, total tau, and GFAP) was found, suggesting no disruption of the integrity of the BBB.

A significant (4.3-fold) increase in plasma concentration of LGALS3 in mTBI patients compared to uninjured subjects was found. While animal studies of severe TBI suggested a long-lasting upregulation of LGALS3 synthesis in the injured brain, a relatively short-lasting increase in plasma levels of LGALS3 was only observed in mTBI patients. LGALS3 has previously been reported to be produced by activated microglia, but its pathophysiological role in neurotrauma is currently unknown. These data showed a positive correlation between plasma levels of LGALS3 and OCLN, suggesting that this proinflammatory mediator might have an adverse effect on BBB function in mTBI. The lack of such correlation in patients with OI can allow for the diagnosis of suspected concussion in the presence of OI.

In summary, four plasma biomarkers for the diagnosis of concussion have been identified. Some of them (MMP9 and/or LGALS3) are targets for therapeutic intervention. Unlike previously reported blood biomarkers, which were the proteins released from the damaged brain cells, the biomarkers described in the present study could readily be measured using standard ELISA. Rapid microfluidics-based immunoassays for these biomarkers are useful for the point-of-care diagnosis in the ED or other relevant environments.

The Inclusion Criteria for the Study:
1. Age between 18 and 65 (inclusive) years
2. Glasgow Coma Scale (GCS) score of 13-15. (Patients for whom the GCS scores were not recorded were awake and able to consent.)
3. Concussion symptoms: subject-reported injury with loss of consciousness and/or two of the following symptoms:
   a. Amnesia
   b. Nausea/vomiting
   c. Headache
   d. Diplopia
   e. Dizziness
   f. Sleepiness
   g. Confusion
   h. Disorientation or sensation of "fogginess"
4. Subject is able to consent
5. Injury occurred less than 24 h before arrival at the Emergency Department The Exclusion Criteria for the Study:
1. Syncope as the cause of the trauma
2. Medical history of cancer, autoimmune disease, active infectious diseases (including HIV and viral hepatitis), and inflammatory conditions (including inflammatory bowel disease)
3. Other concomitant medical issues that require admission to hospital
4. Current treatment with immunomodulator medications (including glucocorticoids), antibiotics, or chemotherapy
5. Alcohol intoxication determined by breathalyzer or blood alcohol content of >0.08%, or clinical suspicion of alcohol intoxication
6. Active psychiatric issues requiring psychiatry evaluation 7. Significant other trauma defined as:
   a. Long bone fracture
   b. Vertebral fracture
   c. Compartment syndrome
   d. Arterial bleeding
   e. Spinal cord injury
   f. Injuries to the lung, heart, and abdominal organs as noted on imaging, or requiring operative intervention or admission to the hospital
   g. Ocular injuries
   h. Burns
   i. Significant soft tissue injuries defined as >10-cm laceration, abrasion, or hematoma Biomarkers Evaluated in this Study Eighteen potential biomarkers were studied. These included proinflammatory mediators tumor necrosis factor-α (TNF-α) and its soluble receptor sTNFR1 (samples diluted 1:5), interleukin-1β (IL-1β), the chemokines CXCL1, CXCL8, and CCL2, colony-stimulating factor 3 (CSF3), osteopontin (SPP1; samples diluted 1:200), galectin 3 (LGALS3; samples diluted 1:5), soluble cell adhesion molecules intercellular adhesion molecule 1 (sICAM1; samples diluted 1:200), sE-selectin (samples diluted 1:20), sP-selectin (samples diluted 1:20), and sL-selectin (samples diluted 1:1000), matrix metalloproteinases (MMPs) MMP2 (samples diluted 1:50), MMP3 (samples diluted 1:100), and MMP9 (samples diluted 1:100), occludin (OCLN), and copeptin.

DuoSet ELISA Development Systems from R&D Systems (Minneapolis, Minn., USA) were used to measure the concentrations of all biomarkers except those of OCLN and copeptin. The levels of OCLN and copeptin were evaluated using the ELISA kits from USCN Life Science (Houston, Tex., USA).

TABLE 2

| Characteristics of enrolled subjects | | | |
|---|---|---|---|
| | Group | | |
| | mTBI (n = 55) | Control (n = 44) | OI (n = 17) |
| Age (years) | 34.0 ± 12.5 | 34.0 ± 11.9 | 41.2 ± 15.2 |
| BMI (kg/m$^2$) | 26.4 ± 4.1 | 25.6 ± 4.5 | 31.5 ± 5.3 |
| Men | 33 (60.0) | 23 (52.3) | 11 (64.7) |
| Race | | | |
| White | 49 (89.1) | 39 (88.6) | 16 (94.1) |
| Black | 3 (5.5) | 1 (2.3) | 1 (5.9) |
| Other | 3 (5.5) | 4 (9.1) | — |
| Ethnicity | | | |
| Non-Hispanic | 41 (74.5) | 40 (90.9) | 14 (82.4) |
| Hispanic | 13 (23.6) | 4 (9.1) | 3 (17.6) |
| Refused/not recorded | 1 (1.8) | — | — |
| Previous TBI | | | |
| Yes | 18 (32.7) | 6 (13.6) | 4 (23.5) |
| Years since last TBI | 9.1 ± 9.6 | 12.5 ± 11.1 | 17.3 ± 16.5 |
| Medical history* | | | |
| None | 31 (56.4) | 31 (70.5) | 12 (70.6) |
| Chronic pain | 6 (10.9) | 2 (4.5) | — |
| Diabetes | 1 (1.8) | — | 2 (11.8) |
| Hypercholesterolemia | 3 (5.5) | 3 (6.8) | 2 (11.8) |
| Hypertension | 4 (7.3) | 3 (6.8) | 4 (23.5) |
| Psychiatric disease | 8 (14.5) | 4 (9.1) | 3 (17.6) |
| Vascular disease (CAD, stroke) | 3 (5.5) | — | — |

TABLE 2-continued

| Characteristics of enrolled subjects | | | |
|---|---|---|---|
| | Group | | |
| | mTBI (n = 55) | Control (n = 44) | OI (n = 17) |
| Medications† | | | |
| None | 24 (43.6) | 24 (54.5) | 12 (70.6) |
| ACE inhibitors/ARB | 4 (7.3) | 2 (4.5) | 1 (5.9) |
| Aspirin | 4 (7.3) | 1 (2.3) | — |
| OCP | 3 (5.5) | 6 (13.6) | 1 (5.9) |
| Statins | 3 (5.5) | 3 (6.8) | 2 (11.8) |
| SSRI/SNRI | 7 (12.7) | 2 (4.5) | 2 (11.8) |
| Mechanism of injury | | | |
| Fall | 15 (27.3) | | |
| Motor vehicle crash | 14 (25.5) | | |
| Sport | 7 (12.7) | | |
| Struck by/against an object | 7 (12.7) | | |
| Assault | 5 (9.1) | | |
| Bicycling | 4 (7.3) | | |
| Pedestrian struck | 3 (5.5) | | |
| GCS on arrival | | | |
| 15 | 28 (50.92) | | |
| 14 | 3 (5.5) | | |
| 13 | — | | |
| Not recorded | 24 (43.6) | | |
| Head CT findings | | | |
| Normal | 25 (45.5) | | |
| Scalp hematoma | 7 (12.7) | | |
| Facial bone fracture | 3 (5.5) | | |
| Sinusitis | 2 (3.6) | | |
| Chronic encephalomalacia | 1 (1.8) | | |
| Intraparenchymal contusion | 1 (1.8) | | |
| CT not performed | 16 (29.1) | | |

Controls = uninjured subjects.
mTBI = subjects who sustained a concussion.
OI = subjects with orthopedic injury.
BMI = body mass index.
CAD = coronary artery disease.
ACE = angiotensin-converting enzyme.
ARB = angiotensin II receptor blockers.
SSRI = Selective serotonin reuptake inhibitors.
SNRI = Serotonin-norepi-nephrine reuptake inhibitors.
OCP = oral contraceptive pills.
GCS = Glasgow Coma Scale.
CT = computed tomography.

*Some subjects had more than one medical problem and were taking more than one medication,
†Only common medications taken are listed. Data are either mean ± SD or n (%).

TABLE 3

Plasma levels of 14 out of 18 proteins evaluated in this study

| Protein | Controls | | | mTBI (1-8 h) | | | mTBI (9-24 h) | | | OI | | |
|---|---|---|---|---|---|---|---|---|---|---|---|---|
| | Mean ± SD | Median | IQR | Mean ± SD | Median | IQR | Mean ± SD | Median | IQR | Mean ± SD | Median | IQR |
| TNF-α (pg/mL) | 252 ± 376 | 24 | 6-481 | 245 ± 559 | 8 | 7-181 | 298 ± 456 | 24 | 8-770 | 340 ± 691 | 8 | 8-48 |
| sTNFR1 (ng/mL) | 0.9 ± 0.5 | 0.8 | 0.6-1.0 | 0.9 ± 0.2 | 1.0 | 0.7-1.2 | 0.7 ± 0.3 | 0.6 | 0.5-1.1 | 0.9 ± 0.2 | 0.9 | 0.8-1.0 |
| IL-1β (pg/mL) | 35 ± 94 | 2 | 2-25 | 30 ± 82 | 2 | 2-10 | 52 ± 131 | 2 | 2-28 | 27 ± 56 | 2 | 2-7 |
| CXCL1 (pg/mL) | 575 ± 687 | 387 | 72-884 | 294 ± 504 | 113 | 16-370 | 711 ± 962 | 224 | 76-1340 | 246 ± 278 | 114 | 49-373 |
| CXCL8 (pg/mL) | 17 ± 41 | 6 | 4-12 | 9 ± 9 | 6 | 4-10 | 12 ± 13 | 7 | 4-14 | 16 ± 26 | 8 | 6-15 |
| CCL2 (pg/mL) | 325 ± 561 | 115 | 67-355 | 136 ± 122 | 94 | 36-213 | 478 ± 883 | 146 | 71-377 | 222 ± 51 | 220 | 168-271 |
| CSF3 (pg/mL) | 24 ± 17 | 17 | 16-27 | 27 ± 12 | 24 | 16-37 | 45 ± 46** | 23 | 16-60 | 36 ± 17 | 31 | 22-18 |
| SPP1 (ng/mL) | 16 ± 11 | 15 | 6-24 | 16 ± 11 | 13 | 6-28 | 28 ± 20 | 29 | 10-36 | 16 ± 9 | 16 | 9-20 |
| sICAM1 (ng/mL) | 118 ± 32 | 113 | 96-135 | 134 ± 31§ | 127 | 113-165 | 95 ± 12 | 99 | 82-106 | 178 ± 103 | 144 | 93-225 |
| sE-selectin (ng/mL) | 14 ± 7 | 14 | 9-18 | 14 ± 5 | 12 | 9-19 | 15 ± 7 | 14 | 9-20 | 19 ± 9 | 17 | 11-25 |
| sP-selectin (ng/mL) | 25 ± 12 | 22 | 18-29 | 34 ± 13 | 33 | 26-38 | 27 ± 12 | 25 | 17-35 | 35 ± 6 | 37 | 28-40 |
| sL-selectin (μg/mL) | 1.5 ± 0.4 | 1.4 | 1.3-1.8 | 1.6 ± 0.3 | 1.7 | 1.3-1.8 | 1.7 ± 0.5 | 1.9 | 1.4-2.0 | 1.2 ± 0.6 | 1.3 | 0.7-1.6 |
| MMP2 (ng/mL) | 84 ± 72 | 62 | 31-119 | 87 ± 28††† | 81 | 68-106 | 106 ± 26 | 97 | 84-118 | 152 ± 52**** | 138 | 130-161 |
| MMP3 (ng/mL) | 15 ± 9 | 12 | 9-22 | 14 ± 6 | 13 | 9-20 | 13 ± 9 | 10 | 6-15 | 9 ± 6 | 6 | 3-15 |

Controls = uninjured subjects.
mTBI (1-8 h) = mTBI patients in whom blood samples were collected between 1 and 8 h post-injury.
mTBI (9-24 h) = mTBI patients in whom blood samples were collected between 9 and 24 h post-injury.
OI = patients with orthopedic injury.
IQR = interquartile range.
**$p < 0.01$,
****$p < 0.0001$ when compared to control.
†††$p < 0.001$ when compared to OI.
§$p < 0.05$ when compared to mTBI (9-24 h).

TABLE 4

Concussion data for the department of emergency medicine
Concussion Data for the Department of Emergency Medicine

| | Year | | | | | | | | | | | | |
|---|---|---|---|---|---|---|---|---|---|---|---|---|---|
| | 2010 | | | 2011 | | | 2012 | | | 2013 | | | |
| Site | Total Number of Concussions | Isolated Concussions | % | Total Number of Concussions | Isolated Concussions | % | Total Number of Concussions | Isolated Concussions | % | Total Number of Concussions | Isolated Concussions | % | |
| RIH | 1129 | 889 | 79 | 1248 | 940 | 75 | 809 | 621 | 77 | 664 | 541 | 81 | |
| TMH | 171 | 145 | 85 | 223 | 209 | 94 | 224 | 203 | 91 | 212 | 191 | 90 | |
| HCH | 683 | 643 | 94 | 826 | 769 | 93 | 757 | 709 | 94 | 740 | 709 | 96 | |

| Site | 2014 Total Number of Concussions | Isolated Concussions | % | 2010-2014 Total Number of Concussions | Isolated Concussions | % |
|---|---|---|---|---|---|---|
| RIH | 765 | 630 | 82 | 4615 | 3621 | 78 |
| TMH | 275 | 253 | 92 | 1105 | 1001 | 91 |
| HCH | 808 | 759 | 94 | 3814 | 3589 | 94 |

RIH = Rhode Islan Hospital
TMH = The Miriam Hospital
HCH = Hasbro Children's Hospital

REFERENCES

1 Faul M, Xu L, Wald M M, Coronado V. Traumatic Brain Injury in the United States: Emergency Department Visits, Hospitalizations and Deaths, 2002-2006. Centers for Disease Control and Prevention, National Center for Injury Prevention and Control, Atlanta, Ga., 2010.
2 Tagliaferri F, Compagnone C, Korsic M, Servadei F, Kraus J. A systematic review of brain injury epidemiology in Europe. *Acta Neurochir (Wien)* 2006; 148: 255-68.
3 Cassidy J D, Carroll L J, Peloso P M, et al. Incidence, risk factors and prevention of mild traumatic brain injury: results of the WHO Collaborating Centre Task Force on Mild Traumatic Brain Injury. *J Rehabil Med* 2004; Suppl. 43: 28-60.
4 Williamson I J, Goodman D. Converging evidence for the under-reporting of concussions in youth ice hockey. *Br J Sports Med* 2006; 40: 128-32.
5 Rigg J L, Mooney S R. Concussions and the military: issues specific to service members. *Pm R* 2011; 3: S380-6.

6 Mondello S, Schmid K, Berger R P, et al. The challenge of mild traumatic brain injury: role of biochemical markers in diagnosis of brain damage. *Med Res Rev* 2014; 34: 503-31.
7 Papa L, Lewis L M, Falk J L, et al. Elevated levels of serum glial fibrillary acidic protein breakdown products in mild and moderate traumatic brain injury are associated with intracranial lesions and neurosurgical intervention. *Ann Emerg Med* 2012; 59: 471-83.
8 Papa L, Lewis L M, Silvestri S, et al. Serum levels of ubiquitin C-terminal hydrolase distinguish mild traumatic brain injury from trauma controls and are elevated in mild and moderate traumatic brain injury patients with intracranial lesions and neurosurgical intervention. *J Trauma Acute Care Surg* 2012; 72: 1335-44.
9 Siman R, Giovannone N, Hanten G, et al. Evidence that the blood biomarker SNTF predicts brain imaging changes and persistent cognitive dysfunction in mild TBI patients. *Front Neurol* 2013; 4: 190.
10 Shahim P, Tegner Y, Wilson D H, et al. Blood biomarkers for brain injury in concussed professional ice hockey players. *JAMA Neurol* 2014; 71: 684-92.
11 McCrory P, Meeuwisse W H, Aubry M, et al. Consensus statement on concussion in sport: the 4th International Conference on Concussion in Sport held in Zurich, November 2012. *Br J Sports Med* 2013; 47: 250-8.
12 Manley G T, Diaz-Arrastia R, Brophy M, et al. Common data elements for traumatic brain injury: recommendations from the Biospecimens and Biomarkers Working Group. *Arch Phys Med Rehabil* 2010; 91: 1667-72.
13 Perez-Polo J R, Rea H C, Johnson K M, et al. Inflammatory consequences in a rodent model of mild traumatic brain injury. *J Neurotrauma* 2013; 30: 727-40.
14 Chodobski A, Zink B J, Szmydynger-Chodobska J. CNS barriers in neurotrauma. In *Vascular Mechanisms in CNS Trauma*, Edited by Eng H Lo, Josephine Lok, MingMing Ning, Michael J Whalen, Springer, New York, 2014, pp. 3-28.
15 Natale J E, Ahmed F, Cernak I, Stoica B, Faden A I. Gene expression profile changes are commonly modulated across models and species after traumatic brain injury. *J Neurotrauma* 2003; 20: 907-27.
16 Liu W, Hendren J, Qin X J, Shen J, Liu K J. Normobaric hyperoxia attenuates early blood-brain barrier disruption by inhibiting MMP-9-mediated occludin degradation in focal cerebral ischemia. *J Neurochem* 2009; 108: 811-20.
17 Szmydynger-Chodobska J, Fox L M, Lynch K M, Zink B J, Chodobski A. Vasopressin amplifies the production of proinflammatory mediators in traumatic brain injury. *J Neurotrauma* 2010; 27: 1449-61.
18 Szmydynger-Chodobska J, Zink B J, Chodobski A. Multiple sites of vasopressin synthesis in the injured brain. *J Cereb Blood Flow Metab* 2011; 31: 47-51.
19 Struck J, Morgenthaler N G, Bergmann A. Copeptin, a stable peptide derived from the vasopressin precursor, is elevated in serum of sepsis patients. *Peptides* 2005; 26: 2500-4.
20 Bazarian J J, Blyth B J, He H, et al. Classification accuracy of serum Apo A-I and S100B for the diagnosis of mild traumatic brain injury and prediction of abnormal initial head computed tomography scan. *J Neurotrauma* 2013; 30: 1747-54.
21 Nygren De Boussard C, Fredman P, Lundin A, Andersson K, Edman G, Borg J. S100 in mild traumatic brain injury. *Brain Inj* 2004; 18: 671-83.
22 Terrando N, Eriksson L I, Ryu J K, et al. Resolving postoperative neuroinflammation and cognitive decline. *Ann Neurol* 2011; 70: 986-95.
23 Dong X Q, Huang M, Yang S B, Yu W H, Zhang Z Y. Copeptin is associated with mortality in patients with traumatic brain injury. *J Trauma* 2011; 71: 1194-8.
24 Roberts D J, Jenne C N, Leger C, et al. A prospective evaluation of the temporal matrix metalloproteinase response after severe traumatic brain injury in humans. J Neurotrauma 2013; 30: 1717-26.
25 Hadass O, Tomlinson B N, Gooyit M, et al. Selective inhibition of matrix metalloproteinase-9 attenuates secondary damage resulting from severe traumatic brain injury. *PLoS One* 2013; 8: e76904.
26 Zetterberg H, Hietala M A, Jonsson M, et al. Neurochemical aftermath of amateur boxing. *Arch Neurol* 2006; 63: 1277-80.
27 Venkatesan C, Chrzaszcz M, Choi N, Wainwright M S. Chronic upregulation of activated microglia immunoreactive for galectin-3/Mac-2 and nerve growth factor following diffuse axonal injury. *J Neuroinflammation* 2010; 7: 32.
28 Lin C C, Wang J H, Wu H W, Lee G B. Microfluidic immunoassays. *JALA Charlottesv Va* 2010; 15: 253-74.

Other Embodiments

While the invention has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank, NCBI, UniProt, or other submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the disclosure encompassed by the appended claims.

What is claimed:

1. A method for identifying concussion or traumatic brain injury in a subject, comprising
   (1) providing a plasma sample from a subject suspected to comprise a concussion or traumatic brain injury;
   (2) performing a reaction in vitro by contacting said plasma sample with an antibody to yield a complex comprising said antibody and a protein selected from the group consisting of copeptin, matrix metallopeptidase 9 (MMP9), lectin, galactose binding, soluble 3 (LGALS3), and occludin (OCLN), wherein said antibody comprises a plurality of antibodies comprising a first antibody that binds to copeptin, a second antibody that binds to MMP9, a third antibody that binds to LGALS3, and a fourth antibody that binds to OCLN;
   (3) detecting said complex,
      wherein a decrease in the level of said complex comprising copeptin compared to a normal control and an increase in the level of said complex comprising MMP9, LGALS3, or OCLN compared to a normal control indicates concussion or traumatic brain injury in said subject wherein said subject has a Glasgow Coma Scale (GCS) score of 13-15.

2. The method of claim 1, wherein said plasma sample is derived from said subject within about 0.1 to about 8 hours of a head injury.

3. The method of claim 1, wherein said antibody comprises a polyclonal antibody or a monoclonal antibody.

4. The method of claim 1, wherein said antibody is bound to a solid support.

5. The method of claim 4, wherein said solid support comprises a strip, a glass, a silicon, a polymer, a bead, or a nanoparticle.

6. The method of claim 1, wherein said complex is identified by a detectable moiety.

7. The method of claim 6, wherein said detectable moiety comprises a fluorescent marker selected from the group consisting of fluorescein isothiocyanate, rhodamine, phycoerythrin, phycocyanin, allophycocyanin, p-phthaldehyde and fluorescamine, and 152 Eu; or wherein the detectable moiety comprises a chemiluminescent compound selected from the group consisting of luminol, isoluminol, theromatic acridinium ester, imidazole, acridinium salt and oxalate ester.

8. The method of claim 1, wherein said traumatic brain injury comprises isolated traumatic brain injury.

9. The method of claim 1, wherein said plasma sample is derived from said subject within about 1 to 8 hours of a head injury.

10. The method of claim 1, wherein said plasma sample is derived from said subject within about 12 hours of a head injury.

11. The method of claim 1, wherein said plasma sample is derived from said subject within about 24 hours of a head injury.

12. A method for identifying concussion or traumatic brain injury in a subject, comprising
   (1) providing a plasma sample from a subject suspected of comprising a concussion or traumatic brain injury;
   (2) performing a reaction in vitro by contacting said plasma sample with an antibody to yield a complex comprising said antibody and a protein selected from the group consisting of copeptin, MMP9, LGALS3, and OCLN, wherein said antibody comprises a plurality of antibodies comprising antibodies for at least three of said proteins; and
   (3) detecting said complex,
      wherein a decrease in the level of said complex comprising copeptin compared to a normal control or an increase in the level of said complex comprising MMP9, LGALS3, or OCLN compared to a normal control indicates concussion or traumatic brain injury in said subject wherein said subject has a Glasgow Coma Scale (GCS) score of 13-15.

13. A method of treating concussion or mild traumatic brain injury (mTBI), comprising:
   (1) providing a test sample from a subject, wherein said test sample comprises a bodily fluid;
   (2) performing a reaction in vitro by contacting said test sample with a binding agent to yield a complex comprising said binding agent and a protein selected from the group consisting of copeptin, MMP9, LGALS3, and OCLN;
   (3) detecting said complex; wherein a decrease in the level of said complex comprising copeptin compared to a normal control and an increase in the level of said complex comprising MMP9, LGALS3, or OCLN compared to a normal control indicates concussion or traumatic brain injury in said subject wherein said subject has a Glasgow Coma Scale (GCS) score of 13-15;

(4) administering to said subject a therapeutically effective amount of a compound that modulates the activity or level of said complex, thereby treating said subject.

14. The method of claim 13, wherein said compound comprises a MMP9 selective inhibitor.

15. The method of claim 14, wherein said MMP9 selective inhibitor comprises 2-[[(4-phenoxyphenyl)sulfonyl]methyl]-Thiirane (SB-3CT) prodrug or a pharmaceutically acceptable salt, ester, metabolite, polymorph or solvate thereof.

16. The method of claim 13, wherein said compound comprises an LGALS3 selective inhibitor.

17. The method of claim 16, wherein said LGALS3 selective inhibitor comprises N-acetyllactosamine, a glycomimetic compound, or a pharmaceutically acceptable salt, ester, prodrug, metabolite, polymorph or solvate thereof.

18. A method of treating concussion or traumatic brain injury in a subject, comprising administering to said subject a therapeutically effective amount of an LGALS3 selective inhibitor.

19. A method for identifying concussion or traumatic brain injury in a subject, comprising
(1) providing a test sample from said subject, wherein said test sample comprises a bodily fluid;
(2) performing a reaction in vitro by contacting said test sample with a binding agent to yield a complex comprising said binding agent and a protein selected from the group consisting of copeptin, MMP9, LGALS3, and OCLN, wherein said binding agent comprises a plurality of binding agents comprising a first binding agent that binds to copeptin, a second binding agent that binds to MMP9, a third binding agent that binds to LGALS3, and a fourth binding agent that binds to OCLN;
(3) detecting said complex,
wherein a decrease in the level of said complex comprising copeptin compared to a normal control and an increase in the level of said complex comprising MMP9, LGALS3, or OCLN compared to a normal control indicates concussion or traumatic brain injury in said subject, wherein said subject has a Glasgow Coma Scale (GCS) score of 13-15 and wherein said method further comprising administering to the subject a therapeutically effective amount of a MMP9 selective inhibitor or an LGALS3 selective inhibitor.

* * * * *

SEQUENCE LISTING

<160> NUMBER OF SEQ ID NOS: 4

<210> SEQ ID NO 1
<211> LENGTH: 164
<212> TYPE: PRT

-continued

<213> ORGANISM: Homo sapiens

<400> SEQUENCE: 1

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
            20                  25                  30

Met Ser Asp Leu Glu Leu Arg Gln Cys Leu Pro Cys Gly Pro Gly Gly
        35                  40                  45

Lys Gly Arg Cys Phe Gly Pro Ser Ile Cys Cys Ala Asp Glu Leu Gly
50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
130                 135                 140

Arg Leu Val Gln Leu Ala Gly Ala Pro Glu Pro Phe Glu Pro Ala Gln
145                 150                 155                 160

Pro Asp Ala Tyr

<210> SEQ ID NO 2
<211> LENGTH: 707
<212> TYPE: PRT
<213> ORGANISM: Homo sapiens

<400> SEQUENCE: 2

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
    50                  55                  60

Lys Ser Leu Gly Pro Ala Leu Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
    130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

-continued

```
Pro Pro Gly Pro Gly Ile Gln Gly Asp Ala His Phe Asp Asp Glu
        195                 200                 205
Leu Trp Ser Leu Gly Lys Gly Val Val Val Pro Thr Arg Phe Gly Asn
210                 215                 220
Ala Asp Gly Ala Ala Cys His Phe Pro Phe Ile Phe Glu Gly Arg Ser
225                 230                 235                 240
Tyr Ser Ala Cys Thr Thr Asp Gly Arg Ser Asp Gly Leu Pro Trp Cys
                245                 250                 255
Ser Thr Thr Ala Asn Tyr Asp Thr Asp Arg Phe Gly Phe Cys Pro
                260                 265                 270
Ser Glu Arg Leu Tyr Thr Gln Asp Gly Asn Ala Asp Gly Lys Pro Cys
                275                 280                 285
Gln Phe Pro Phe Ile Phe Gln Gly Gln Ser Tyr Ser Ala Cys Thr Thr
        290                 295                 300
Asp Gly Arg Ser Asp Gly Tyr Arg Trp Cys Ala Thr Thr Ala Asn Tyr
305                 310                 315                 320
Asp Arg Asp Lys Leu Phe Gly Phe Cys Pro Thr Arg Ala Asp Ser Thr
                325                 330                 335
Val Met Gly Gly Asn Ser Ala Gly Glu Leu Cys Val Phe Pro Phe Thr
                340                 345                 350
Phe Leu Gly Lys Glu Tyr Ser Thr Cys Thr Ser Glu Gly Arg Gly Asp
                355                 360                 365
Gly Arg Leu Trp Cys Ala Thr Thr Ser Asn Phe Asp Ser Asp Lys Lys
        370                 375                 380
Trp Gly Phe Cys Pro Asp Gln Gly Tyr Ser Leu Phe Leu Val Ala Ala
385                 390                 395                 400
His Glu Phe Gly His Ala Leu Gly Leu Asp His Ser Ser Val Pro Glu
                405                 410                 415
Ala Leu Met Tyr Pro Met Tyr Arg Phe Thr Glu Gly Pro Pro Leu His
                420                 425                 430
Lys Asp Asp Val Asn Gly Ile Arg His Leu Tyr Gly Pro Arg Pro Glu
        435                 440                 445
Pro Glu Pro Arg Pro Pro Thr Thr Thr Pro Gln Pro Thr Ala Pro
450                 455                 460
Pro Thr Val Cys Pro Thr Gly Pro Pro Thr Val His Pro Ser Glu Arg
465                 470                 475                 480
Pro Thr Ala Gly Pro Thr Gly Pro Pro Ser Ala Gly Pro Thr Gly Pro
                485                 490                 495
Pro Thr Ala Gly Pro Ser Thr Ala Thr Thr Val Pro Leu Ser Pro Val
                500                 505                 510
Asp Asp Ala Cys Asn Val Asn Ile Phe Asp Ala Ile Ala Glu Ile Gly
                515                 520                 525
Asn Gln Leu Tyr Leu Phe Lys Asp Gly Lys Tyr Trp Arg Phe Ser Glu
        530                 535                 540
Gly Arg Gly Ser Arg Pro Gln Gly Pro Phe Leu Ile Ala Asp Lys Trp
545                 550                 555                 560
Pro Ala Leu Pro Arg Lys Leu Asp Ser Val Phe Glu Glu Arg Leu Ser
                565                 570                 575
Lys Lys Leu Phe Phe Phe Ser Gly Arg Gln Val Trp Val Tyr Thr Gly
                580                 585                 590
Ala Ser Val Leu Gly Pro Arg Arg Leu Asp Lys Leu Gly Leu Gly Ala
                595                 600                 605
Asp Val Ala Gln Val Thr Gly Ala Leu Arg Ser Gly Arg Gly Lys Met
```

```
                    610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                    645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
            690                 695                 700

Pro Glu Asp
705

<210> SEQ ID NO 3
<211> LENGTH: 250
<212> TYPE: PRT
<213> ORGANISM: Homo sapiens

<400> SEQUENCE: 3

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
                20                  25                  30

Ala Gly Gly Tyr Pro Gly Ala Ser Tyr Pro Gly Ala Tyr Pro Gly Gln
            35                  40                  45

Ala Pro Pro Gly Ala Tyr Pro Gly Gln Ala Pro Pro Gly Ala Tyr Pro
        50                  55                  60

Gly Ala Pro Gly Ala Tyr Pro Gly Ala Pro Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Thr Gly Ala Tyr Pro Ala Thr Gly Pro Tyr Gly Ala Pro Ala Gly
                100                 105                 110

Pro Leu Ile Val Pro Tyr Asn Leu Pro Leu Pro Gly Gly Val Val Pro
            115                 120                 125

Arg Met Leu Ile Thr Ile Leu Gly Thr Val Lys Pro Asn Ala Asn Arg
130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 4
<211> LENGTH: 522
```

<212> TYPE: PRT
<213> ORGANISM: Homo sapiens

<400> SEQUENCE: 4

Met Ser Ser Arg Pro Leu Glu Ser Pro Pro Tyr Arg Pro Asp Glu
1               5                   10                  15

Phe Lys Pro Asn His Tyr Ala Pro Ser Asn Asp Ile Tyr Gly Glu
            20                  25                  30

Met His Val Arg Pro Met Leu Ser Gln Pro Ala Tyr Ser Phe Tyr Pro
        35                  40                  45

Glu Asp Glu Ile Leu His Phe Tyr Lys Trp Thr Ser Pro Pro Gly Val
50                  55                  60

Ile Arg Ile Leu Ser Met Leu Ile Ile Val Met Cys Ile Ala Ile Phe
65                  70                  75                  80

Ala Cys Val Ala Ser Thr Leu Ala Trp Asp Arg Gly Tyr Gly Thr Ser
                85                  90                  95

Leu Leu Gly Gly Ser Val Gly Tyr Pro Tyr Gly Gly Ser Gly Phe Gly
            100                 105                 110

Ser Tyr Gly Ser Gly Tyr Gly Tyr Gly Tyr Gly Tyr Gly Tyr
        115                 120                 125

Gly Gly Tyr Thr Asp Pro Arg Ala Ala Lys Gly Phe Met Leu Ala Met
130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
                165                 170                 175

Ile Val Ser Ala Ile Leu Gly Ile Met Val Phe Ile Ala Thr Ile Val
            180                 185                 190

Tyr Ile Met Gly Val Asn Pro Thr Ala Gln Ser Ser Gly Ser Leu Tyr
        195                 200                 205

Gly Ser Gln Ile Tyr Ala Leu Cys Asn Gln Phe Tyr Thr Pro Ala Ala
210                 215                 220

Thr Gly Leu Tyr Val Asp Gln Tyr Ser Tyr His Tyr Cys Val Val Asp
225                 230                 235                 240

Pro Gln Glu Ala Ile Ala Ile Val Leu Gly Phe Met Ile Ile Val Ala
                245                 250                 255

Phe Ala Leu Ile Ile Phe Phe Ala Val Lys Thr Arg Arg Lys Met Asp
            260                 265                 270

Arg Tyr Asp Lys Ser Asn Ile Leu Trp Asp Lys Glu His Ile Tyr Asp
        275                 280                 285

Glu Gln Pro Pro Asn Val Glu Glu Trp Val Lys Asn Val Ser Ala Gly
290                 295                 300

Thr Gln Asp Val Pro Ser Pro Ser Asp Tyr Val Glu Arg Val Asp
305                 310                 315                 320

Ser Pro Met Ala Tyr Ser Ser Asn Gly Lys Val Asn Asp Lys Arg Phe
                325                 330                 335

Tyr Pro Glu Ser Ser Tyr Lys Ser Thr Pro Val Pro Glu Val Val Gln
            340                 345                 350

Glu Leu Pro Leu Thr Ser Pro Val Asp Asp Phe Arg Gln Pro Arg Tyr
        355                 360                 365

Ser Ser Gly Gly Asn Phe Glu Thr Pro Ser Arg Ala Pro Ala Lys
370                 375                 380

Gly Arg Ala Gly Arg Ser Lys Arg Thr Glu Gln Asp His Tyr Glu Thr
385                 390                 395                 400

```
Asp Tyr Thr Thr Gly Gly Glu Ser Cys Asp Glu Leu Glu Glu Asp Trp
            405                 410                 415

Ile Arg Glu Tyr Pro Pro Ile Thr Ser Asp Gln Gln Arg Gln Leu Tyr
                420                 425                 430

Lys Arg Asn Phe Asp Thr Gly Leu Gln Glu Tyr Lys Ser Leu Gln Ser
            435                 440                 445

Glu Leu Asp Glu Ile Asn Lys Glu Leu Ser Arg Leu Asp Lys Glu Leu
        450                 455                 460

Asp Asp Tyr Arg Glu Glu Ser Glu Glu Tyr Met Ala Ala Ala Asp Glu
465                 470                 475                 480

Tyr Asn Arg Leu Lys Gln Val Lys Gly Ser Ala Asp Tyr Lys Ser Lys
                485                 490                 495

Lys Asn His Cys Lys Gln Leu Lys Ser Lys Leu Ser His Ile Lys Lys
                500                 505                 510

Met Val Gly Asp Tyr Asp Arg Gln Lys Thr
            515                 520
```